United States Patent
Ikehata et al.

(10) Patent No.: US 11,579,063 B2
(45) Date of Patent: Feb. 14, 2023

(54) CELL CULTURE APPARATUS, IMAGING UNIT, AND CULTURE MONITORING METHOD

(71) Applicant: FUJIFILM CORPORATION, Tokyo (JP)

(72) Inventors: Kosuke Ikehata, Kanagawa (JP); Kazuo Onishi, Kanagawa (JP); Tomoyuki Shimoda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 543 days.

(21) Appl. No.: 16/508,329

(22) Filed: Jul. 11, 2019

(65) Prior Publication Data

US 2019/0331581 A1 Oct. 31, 2019

Related U.S. Application Data

(63) Continuation of application No. PCT/JP2018/002569, filed on Jan. 26, 2018.

(30) Foreign Application Priority Data

Jan. 31, 2017 (JP) .............................. JP2017-015997

(51) Int. Cl.
*G01N 15/02* (2006.01)
*G01N 30/00* (2006.01)
(Continued)

(52) U.S. Cl.
CPC ......... *G01N 15/0227* (2013.01); *C12M 23/58* (2013.01); *C12M 41/06* (2013.01);
(Continued)

(58) Field of Classification Search
CPC ...... C12M 23/06; C12M 23/58; C12M 25/16; C12M 41/06; C12M 41/14; C12M 41/32;
(Continued)

(56) References Cited

U.S. PATENT DOCUMENTS 4,338,024 A 7/1982 Bolz
9,738,861 B2 8/2017 Nakatsuji et al.
(Continued)

FOREIGN PATENT DOCUMENTS

JP S57-500995 A 6/1982
JP H06-308015 A 11/1994
(Continued)

OTHER PUBLICATIONS

International Search Report issued in International Application No. PCT/JP2018/002569 dated Mar. 20, 2018.
(Continued)

*Primary Examiner* — Lydia Edwards
(74) *Attorney, Agent, or Firm* — Solaris Intellectual Property Group, PLLC

(57) ABSTRACT

A cell culture apparatus includes a flow passage in which cell suspension containing at least one of cells or cell masses as granular bodies is to flow, and an imaging unit that is provided in a middle of the flow passage and continuously images the plurality of granular bodies contained in the cell suspension to acquire a plurality of images while the cell suspension flows in the flow passage.

20 Claims, 16 Drawing Sheets

(51) Int. Cl.
    *C12M 1/00* (2006.01)
    *C12M 1/34* (2006.01)
    *C12M 1/36* (2006.01)
    *G01N 15/00* (2006.01)

(52) U.S. Cl.
    CPC ............ *C12M 41/14* (2013.01); *C12M 41/32* (2013.01); *C12M 41/36* (2013.01); *C12M 41/48* (2013.01); *C12M 43/00* (2013.01); *G01N 2015/0065* (2013.01); *G01N 2015/035* (2013.01)

(58) Field of Classification Search
    CPC ...... C12M 41/36; C12M 41/48; C12M 43/00; G01N 15/0227; G01N 15/06; G01N 2015/0053; G01N 2015/0065; G01N 2015/035; G01N 2015/0693
    See application file for complete search history.

(56) References Cited

U.S. PATENT DOCUMENTS

| | | | |
|---|---|---|---|
| 2016/0060588 A1 | 3/2016 | Nakatsuji et al. | |
| 2016/0109372 A1* | 4/2016 | Wanders | G01N 21/85 |
| | | | 356/40 |
| 2017/0159003 A1 | 6/2017 | Shimase et al. | |
| 2017/0191019 A1 | 7/2017 | Kawarai et al. | |
| 2017/0191021 A1 | 7/2017 | Wakui | |

FOREIGN PATENT DOCUMENTS

| | | |
|---|---|---|
| JP | H07-049301 A | 2/1995 |
| JP | 2006-320226 A | 11/2006 |
| JP | 2007-97411 A | 4/2007 |
| JP | 2008-212017 A | 9/2008 |
| JP | 2010-99011 A | 5/2010 |
| JP | 2016-59329 A | 4/2016 |
| JP | 2016-154450 A | 9/2016 |
| WO | 2014/136581 A1 | 9/2014 |
| WO | 2015/107667 A1 | 7/2015 |
| WO | 2016/013392 A1 | 1/2016 |
| WO | 2016/013394 A1 | 1/2016 |
| WO | 2016/013395 A1 | 1/2016 |

OTHER PUBLICATIONS

Written Opinion of the ISA issued in International Application No. PCT/JP2018/002569 dated Mar. 20, 2018.
International Preliminary Report on Patentability issued in International Application No. PCT/JP2018/002569 dated Apr. 4, 2019.

* cited by examiner

FIG. 8A

| PARTICLE SIZE RANGE [μm] | REPRESENTATIVE PARTICLE SIZE [μm] | INTEGRATED NUMBER Na [PIECE] | ACTUAL NUMBER Nb [PIECE] |
|---|---|---|---|
| TO 10 | 5 | a1 | b1 |
| 10 TO 20 | 15 | a2 | b2 |
| 20 TO 30 | 25 | a3 | b3 |
| 30 TO 40 | 35 | a4 | b4 |
| 40 TO 50 | 45 | a5 | b5 |
| 50 TO 60 | 55 | a6 | b6 |
| 60 TO 70 | 65 | a7 | b7 |
| ⋮ | ⋮ | ⋮ | ⋮ |

FIG. 8B

| ROUNDNESS | INTEGRATED NUMBER Na [PIECE] | ACTUAL NUMBER Nb [PIECE] |
|---|---|---|
| 1 | c1 | d1 |
| 0.99 TO 1 | c2 | d2 |
| 0.98 TO 0.99 | c3 | d3 |
| 0.97 TO 0.98 | c4 | d4 |
| 0.96 TO 0.97 | c5 | d5 |
| 0.95 TO 0.96 | c6 | d6 |
| 0.94 TO 0.95 | c7 | d7 |
| ⋮ | ⋮ | ⋮ |

PARTICLE SIZE DISTRIBUTIONS
BEFORE AND AFTER DIVISION TREATMENT

PARTICLE SIZE DISTRIBUTIONS
BEFORE AND AFTER DIVISION TREATMENT

CELL CULTURE APPARATUS, IMAGING UNIT, AND CULTURE MONITORING METHOD

CROSS-REFERENCE TO RELATED APPLICATIONS

This application is a continuation application of International Application No. PCT/JP2018/002569, filed Jan. 26, 2018, the disclosure of which is incorporated herein by reference in its entirety. Further, this application claims priority from Japanese Patent Application No. 2017-015997, filed Jan. 31, 2017, the disclosure of which is incorporated herein by reference in its entirety.

BACKGROUND

1. Technical Field

A technique of the disclosure relates to a cell culture apparatus, an imaging unit, and a culture monitoring method.

2. Related Art

A cell culture apparatus including means for imaging cells, which are being cultured, is known.

For example, JP2016-154450A discloses a state analysis system that images a specific area of a suspended culture solution where cell masses having a plurality of different particle sizes are present and performs image analysis for the imaged specific area. The state analysis system estimates a base mixing ratio of each base information about the distribution feature quantity of cell masses by image analysis, and calculates the particle size distribution of cell masses over the entire suspension culture vessel and the total number of the cell masses over the entire suspension culture vessel on the basis of the estimated mixing ratio.

JP2010-099011A discloses a cell culture apparatus comprising imaging means for imaging a second culture vessel into which cell suspension containing cells collected from a first culture vessel is injected, stirring means for stirring the cell suspension by oscillating the second culture vessel, and control means for controlling the stirring means so that the second culture vessel is oscillated with a stirring operation determined on the basis of an image taken by the imaging means.

JP2006-320226A discloses a cell culture apparatus that performs work for seeding cells by controlling and oscillating a cell culture vessel using a drive device and images the cell culture vessel by an imaging device to acquire a state where the cells are seeded.

WO2015/107667A discloses an automatic culture apparatus comprising a culture vessel, an imaging unit that takes the images of cells held by the culture vessel, and a control unit that allows the quality of regeneration to be evaluated on the basis of information on the images of cells, which correspond to different culture periods, of a plurality of divided areas of the images of cells taken by the imaging unit.

SUMMARY

In the suspension culture for regenerative medicine, a plurality of cells aggregate and form spherical cell masses and the particle sizes of the cell masses are gradually increased with the proliferation of cells. Since it is difficult for nutrition and oxygen to reach the central portions of the cell masses in a case where the particle sizes of the cell masses are too large, cells positioned at the central portions of the cell masses become necrotic. Accordingly, in a stage where the particle sizes of the cell masses reach a certain size, division treatment (subculture treatment) for dividing the cell masses into cell masses having a smaller particle size is necessary in the suspension culture for regenerative medicine. Since the cell masses, which are divided and are reduced in a particle size, are improved again in terms of the absorption efficiency of nutrition and oxygen, the particle sizes of the cell masses are increased as cells are proliferated with time. An increase in the particle size of a cell mass means an increase in the number of cells included in the cell mass. It is necessary to grasp how much the particle sizes of cell masses have grown to grasp an appropriate timing when the cell masses are to be divided. It is possible to grasp how much the particle sizes of the cell masses have grown from the particle size distribution of cell masses.

Further, for the culture of cells, a used culture solution of which the nutrition has been consumed needs to be regularly replaced with a fresh culture solution during a culture period. In the replacement of a culture solution, the used culture solution needs to be replaced with a fresh culture solution in a state where cell masses remain in a system. In this case, it is important for the subsequent normal proliferation of cells that dead cells are to be discharged together with the used culture solution. Concentration treatment for separating a used culture solution from cells by a filter to increase the concentration of the cells in the culture solution is performed in the treatment for replacing a culture solution. The particle size distribution of cell masses after the concentration treatment needs to be grasped to grasp whether or not the concentration treatment is appropriately performed. After that, dilution/mixing treatment for adding a fresh culture solution, which is nutritious, to the concentrated cells and mixing the fresh culture solution and the cells is performed. An object of the dilution/mixing treatment is to uniformly mix a concentrated culture solution containing cells and a fresh culture solution at a predetermined ratio.

In the mass culture of cells, each of the subculture treatment, the concentration treatment, and the dilution/mixing treatment is an important process influencing the success or failure of the culture of cells, but whether or not culture is smoothly performed in the culture vessel is more important than each treatment. The temporal change of the number of cells in the culture vessel or the particle size distribution of cell masses may be grasped to grasp the smoothness of culture.

Knowing the particle size distribution of cells or cell masses, which are being cultured, is very useful in the mass culture of cells as described above. That is, the state of culture can be grasped at a glance in a case where the temporal change of the particle size distribution of cell masses, which are being cultured, is grasped. Further, the state of the division treatment (subculture treatment) can be grasped from the comparison of the particle size distributions of cell masses before and after the division treatment (subculture treatment). Furthermore, the state of the concentration treatment and the state of the dilution/mixing treatment can be grasped in a case where the particle size distribution of the cell masses after the concentration treatment and the particle size distribution of the cell masses after the dilution/mixing treatment are grasped.

An existing method of acquiring the particle size distribution of the cell masses includes collecting cell masses from each culture solution, visually observing the cell masses by a microscope, and counting the number of cell masses having each particle size. However, this method has the following problems.

A first problem is that an act for collecting cell masses increases a risk causing biological contamination in the culture apparatus.

A second problem is that a lot of efforts and time are required to count cell masses. Since many cell masses are included in the field of view of a microscope, it is not easy to manually measure the particle size of each of the cell masses while focusing on each of the cell masses and it is difficult to measure many cell masses. Accordingly, there is no choice but to collect a small amount of a culture solution containing cell masses.

A third problem is that measurement using the collection of a small amount of the culture solution may not correctly represent all the culture solution and the result of the measurement always has inaccuracy.

A fourth problem is that cell masses collected for measurement cannot continue to be cultured and cells are consumed every measurement.

Further, a method of observing the inside of a culture vessel with an imaging device to grasp the state of culture is also proposed. According to this method, there is no risk of biological contamination, efforts and time can be reduced, and cells are not consumed. However, many cells are necessary in regenerative medicine, a culture vessel has a volume of, for example, 2 L to 10 L, and a measurement method using the imaging device in the related art uses cell masses having a volume of about 0.01 L as an object to be observed. Accordingly, there is a concern that a measurement error may be increased by 200 times to 1000 times. Since there is also a concern that a large culture vessel having a volume of 2 L to 10 L may have the problem of locality where an area where cells are present is on one side, imaging devices corresponding to at least ten sets are necessary to accurately grasp the entire state of culture. For this reason, costs are increased.

Other problems of the method of observing cells or cell masses in the related art are caused by observation means. That is, in the observation of cells, a phase-contrast microscope is usually used to obtain contrast and large-aperture angle imaging is performed to obtain high resolution. For this reason, since the depth of focus is reduced, only cells or cell masses present on a focused surface can be observed in a case where liquid having a large depth is to be observed. That is, this problem includes the problem of locality where only a part of the culture solution can be measured. The above-mentioned techniques in the related art are not techniques that can solve the above-mentioned problems.

For example, in a case where illumination light is applied to the specific area from the side surface in a cylindrical culture vessel disclosed in JP2016-154450A and the specific area is imaged by an imaging device in a direction orthogonal to the traveling direction of the illumination light, the illumination light is not applied to areas other than the specific area. Accordingly, noises caused by cells, which are positioned on the inner side (more distant) than the specific area, can be prevented, but cells floating between the specific area and the imaging device form shadows. For this reason, as the concentration of cells of the cell suspension is higher, an influence of cells on measurement accuracy is higher. Further, since an interface between a culture vessel (generally, the refractive index of water is 1.3 and the refractive index of a resin or glass is also changed depending on a physical property but is larger than 1) and air (of which the refractive index is 1) is a curved surface in a case where the culture vessel has a cylindrical shape, distortion caused by the surface shape of the vessel is generated on the image of the specific area to be imaged by the imaging device. For this reason, to obtain the accurate size of a cell, it is necessary to narrow the field of view of the imaging device to reduce the influence of distortion on an image.

The technique of the disclosure has been made in consideration of the above-mentioned circumstances, and an object of the technique of the disclosure is to perform the measurement of cultured cells where an act for collecting cells is unnecessary and most of cell suspension is used as an object to be imaged.

A cell culture apparatus according to the technique of the disclosure comprises a flow passage in which cell suspension containing at least one of cells or cell masses as granular bodies is to flow, and an imaging unit that is provided in a middle of the flow passage and continuously images the plurality of granular bodies contained in the cell suspension to acquire a plurality of images while the cell suspension flows in the flow passage.

The cell culture apparatus may further comprise a derivation unit that derives statistical data on the plurality of granular bodies on the basis of the plurality of images. The statistical data may include at least one of the number of granular bodies being in each predetermined particle size range, the number of granular bodies being in each predetermined particle size range per unit volume, or the number of granular bodies being in each predetermined roundness range among the plurality of granular bodies, or the total number of the cells forming the granular bodies.

The imaging unit may include a flow cell through which the cell suspension is to pass, and an imaging part that includes a plurality of imaging elements of which imaging fields of view are set to the flow cell.

The flow cell may include an inlet into which the cell suspension is to flow, an outlet out of which the cell suspension flowing in from the inlet is to flow, and a flat flow passage that is provided between the inlet and the outlet and is formed of a member of which a thickness in an optical axis direction of the imaging part is smaller than thicknesses of the inlet and the outlet in the optical axis direction and which has light transmittance. The flat flow passage may be formed of a member of which a thickness in an optical axis direction of the imaging part is smaller than a length in a width direction crossing a flow direction of the cell suspension flowing in the flow cell and which has light transmittance. The imaging fields of view of the imaging part may be set to the flat flow passage.

It is preferable that the thickness of the flat flow passage of the flow cell in the optical axis direction is uniform. Further, it is preferable that the entire area of the flat flow passage in a width direction crossing a flow direction of the cell suspension is in the imaging fields of view of the plurality of imaging elements.

The imaging part may include an area sensor that includes the plurality of imaging elements, and a first telecentric lens that is provided on a light-incident side of the area sensor.

The imaging unit may further include an illumination part that irradiates the flat flow passage with illumination light. The illumination part may include a light source that emits the illumination light, and a second telecentric lens that is provided on a light-emitting side of the light source. It is preferable that an optical axis of the first telecentric lens and an optical axis of the second telecentric lens coincide with each other.

It is preferable that the imaging part images each of the plurality of granular bodies, which pass through the inside of the flow cell, one or more times.

It is preferable that a maximum speed of the cell suspension flowing in the flat flow passage is equivalent to maximum speeds of the cell suspension flowing through the inlet and the outlet.

The cell culture apparatus may further comprise at least one vessel which is connected to the flow passage and in which the cell suspension is stored, at least one treatment unit that is connected to the flow passage and performs treatment on the cell suspension, and a pump that generates the flow of cell suspension in the flow passage.

The cell culture apparatus may include a dividing unit, which divides the cell masses contained in the cell suspension, as the treatment unit. In this case, the imaging unit may be provided on each of an upstream side and a downstream side of the dividing unit.

The cell culture apparatus may include a concentrating unit, which concentrates the cell suspension, as the treatment unit. In this case, the imaging unit may be provided on each of an upstream side and a downstream side of the concentrating unit.

The cell culture apparatus may include a mixing unit, which mixes the cell suspension, as the treatment unit. In this case, the imaging unit may be provided on a downstream side of the mixing unit.

In the cell culture apparatus, the pump and the imaging unit may operate while being interlocked with each other.

An imaging unit according to a first aspect of the technique of the disclosure comprises: an imaging part that includes a plurality of imaging elements; and a flow cell that includes an inlet into which cell suspension containing at least one of cells or cell masses as granular bodies is to flow, an outlet out of which the cell suspension flowing in from the inlet is to flow, and a flat flow passage provided between the inlet and the outlet. In the imaging unit according to the first aspect of the technique of the disclosure, the flat flow passage is formed of a member of which a thickness in an optical axis direction of the imaging part is smaller than thicknesses of the inlet and the outlet in the optical axis direction and which has light transmittance, and an imaging field of view of the imaging part is set to the flat flow passage.

An imaging unit according to a second aspect of the technique of the disclosure comprises: an imaging part that includes a plurality of imaging elements; and a flow cell that includes an inlet into which cell suspension containing at least one of cells or cell masses as granular bodies is to flow, an outlet out of which the cell suspension flowing in from the inlet is to flow, and a flat flow passage provided between the inlet and the outlet. In the imaging unit according to the second aspect of the technique of the disclosure, the flat flow passage is formed of a member of which a thickness in an optical axis direction of the imaging part is smaller than a length in a width direction crossing a flow direction of the cell suspension flowing in the flow cell and which has light transmittance, and an imaging field of view of the imaging part is set to the flat flow passage.

A culture monitoring method according to the technique of the disclosure comprises continuously imaging a plurality of granular bodies contained in cell suspension passing through a flow passage to acquire a plurality of images while the cell suspension containing at least one of cells or cell masses as the granular bodies flows in the flow passage, and acquiring statistical data on the plurality of granular bodies on the basis of the plurality of images to monitor a state in which cells are cultured.

In the culture monitoring method, the statistical data may include at least one of the number of granular bodies being in each predetermined particle size range, the number of granular bodies being in each predetermined particle size range per unit volume, or the number of granular bodies being in each predetermined roundness range among the plurality of granular bodies, or the total number of the cells forming the granular bodies.

In the culture monitoring method, the numbers of the plurality of granular bodies being in each predetermined particle size range before and after division treatment for dividing the cell masses contained in the cell suspension may be acquired as the statistical data. The division treatment may include treatment for making the cell suspension pass through a mesh at a predetermined speed of flow. In this case, the speed of flow may be determined on the basis of the statistical data.

In the culture monitoring method, the number of the plurality of granular bodies being in each predetermined particle size range after concentration treatment for concentrating the cell suspension may be acquired as the statistical data. The concentration treatment may include treatment for separating the cell suspension a plurality of times by a filter membrane. In this case, completion of the concentration treatment may be determined on the basis of the statistical data. Further, clogging of the filter membrane may be detected on the basis of the statistical data.

In the culture monitoring method, a temporal change of density of the plurality of granular bodies after the mixing treatment for mixing the cell suspension may be acquired as the statistical data. The mixing treatment may include treatment for making the cell suspension pass through a mixer a plurality of times to mix the plurality of granular bodies and a culture medium. In this case, completion of the mixing treatment may be determined on the basis of the statistical data.

In the culture monitoring method, the number of the plurality of granular bodies being in each predetermined particle size range at a predetermined timing during a culture period may be acquired as the statistical data.

According to the technique of the disclosure, it is possible to realize the measurement of cultured cells where an act for collecting cells is unnecessary and most of cell suspension is used as an object to be imaged.

BRIEF DESCRIPTION OF THE DRAWINGS

Exemplary embodiments according to the technique of the present disclosure will be described in detail based on the following figures, wherein:

FIG. 8A is a diagram showing an example of an output form of particle size distribution as statistical data that are derived by the image analyzer according to the embodiment of the technique of the disclosure;

FIG. 8B is a diagram showing an example of an output form of roundness distribution as statistical data that are derived by the image analyzer according to the embodiment of the technique of the disclosure;

DETAILED DESCRIPTION

Figure 1:
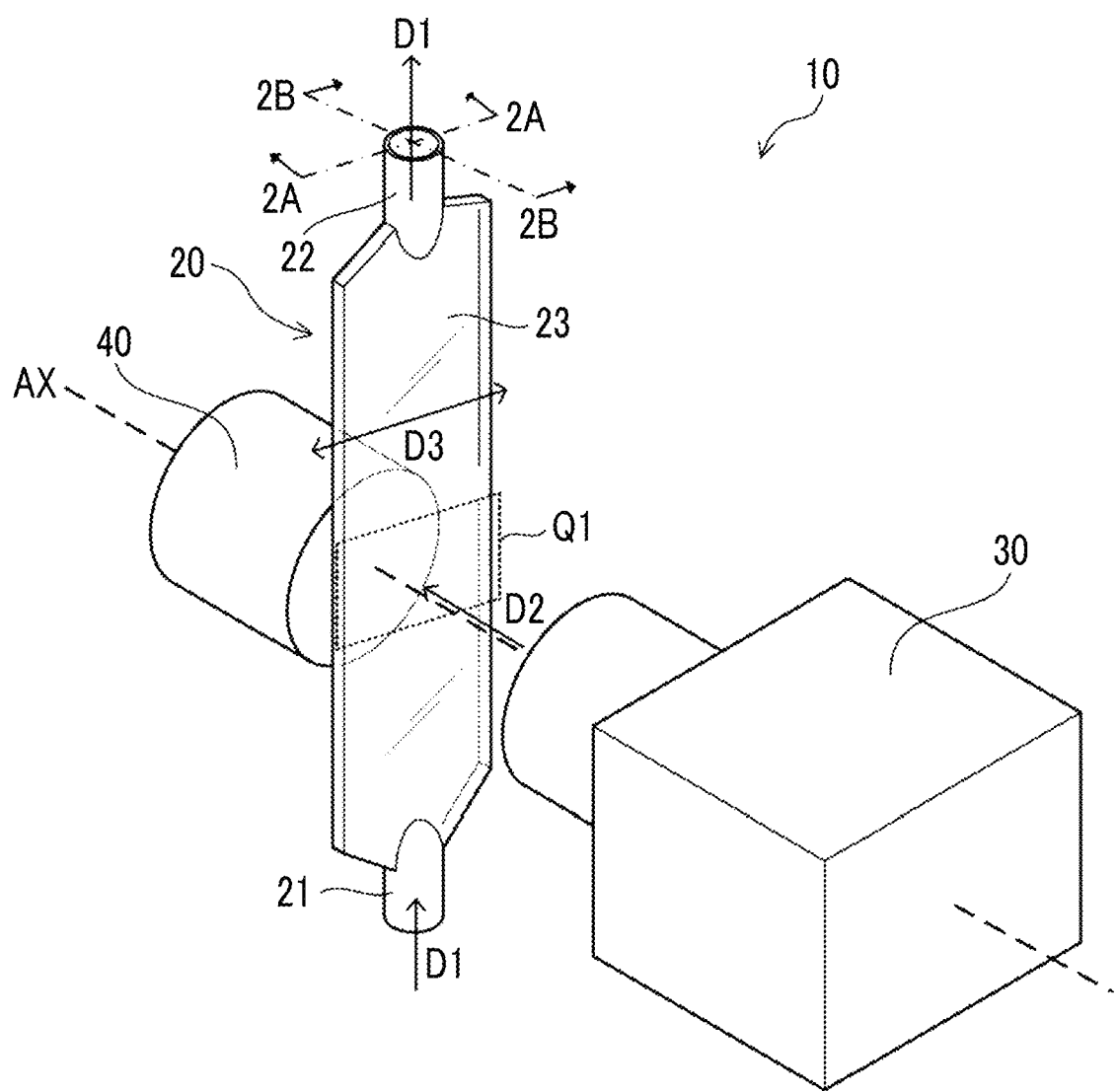
FIG. 1 is a perspective view showing the configuration of an imaging unit according to an embodiment of a technique of the disclosure.

An example of an embodiment of a technique of the disclosure will be described below with reference to the drawings. In the respective drawings, the same or equivalent components and portions will be denoted by the same reference numerals.

FIG. 1 is a perspective view showing the configuration of an imaging unit 10 according to an embodiment of a technique of the disclosure. The imaging unit 10 is provided in the middle of a flow passage in which cell suspension is to flow, and continuously images at least one of cells or cell masses (hereinafter, referred to as cells and the like) contained in the cell suspension to acquire a plurality of images while the cell suspension flows in the flow passage. The plurality of images, which are acquired by the imaging unit 10, are used to derive statistical data on a plurality of cells and the like. The statistical data can include at least one of the number (particle size distribution) of cells being in each predetermined particle size range, the number (density distribution) of cells being in each predetermined particle size range per unit volume or the number (roundness distribution) of cells being in each predetermined roundness range among the plurality of cells and the like contained in cell suspension, or the total number of the cells. A cell mass is a spherical aggregate that is formed in a case where a plurality of cells aggregate. The imaging unit 10 includes a flow cell 20, an imaging part 30, and an illumination part 40.

The flow cell 20 forms a flow passage through which cell suspension containing cells and the like is to pass. Since the entire flow cell 20 is made of a light-transmitting material, such as an optical glass or plastic, cells and the like passing through the inside of the flow cell 20 can be imaged by the imaging part 30 disposed outside the flow cell 20.

The flow cell 20 includes an inlet 21 into which cell suspension is to flow and an outlet 22 out of which the cell suspension flowing in from the inlet 21 is to flow. That is, the cell suspension passing through the inside of the flow cell 20 flows in a flow direction D1 that is indicated in FIG. 1 by an arrow. In terms of easily counting the number of cells and the like, it is preferable that the flow of the cell suspension passing through the inside of the flow cell 20 is laminar flow.

The inlet 21 and the outlet 22 have, for example, a tubular shape. The inlet 21 and the outlet 22 may have the shape of a polygonal tube, such as a triangular tube or a quadrangular tube.

The flow cell 20 includes a flat flow passage 23 provided between the inlet 21 and the outlet 22, and the imaging field Q1 of view of the imaging part 30 is set to the flat flow passage 23. An optical axis direction D2 of the imaging part 30 is set to a direction orthogonal to the flow direction D1 of cell suspension. An optical axis AX of the imaging part 30 is shown in FIG. 1 by a broken line.

Figure 2A:
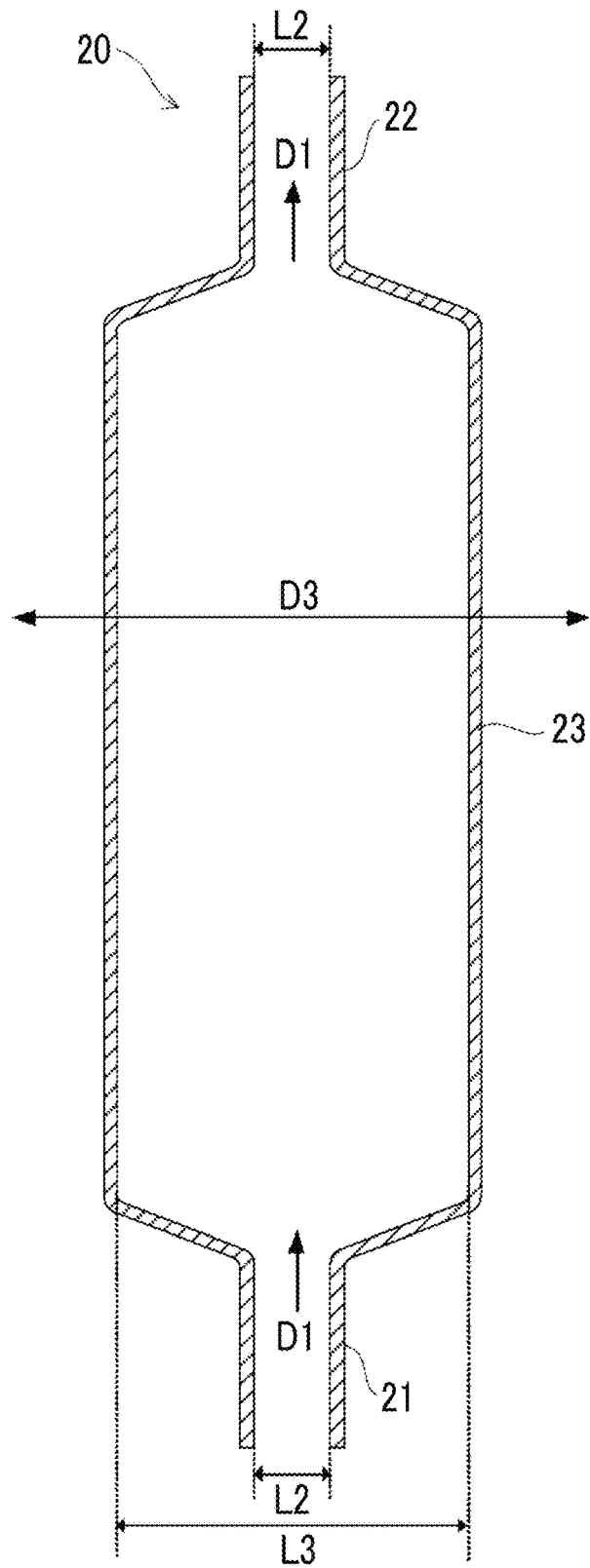
FIG. 2A is a cross-sectional view of a flow cell taken along line 2A-2A of FIG. 1.
Figure 2B:
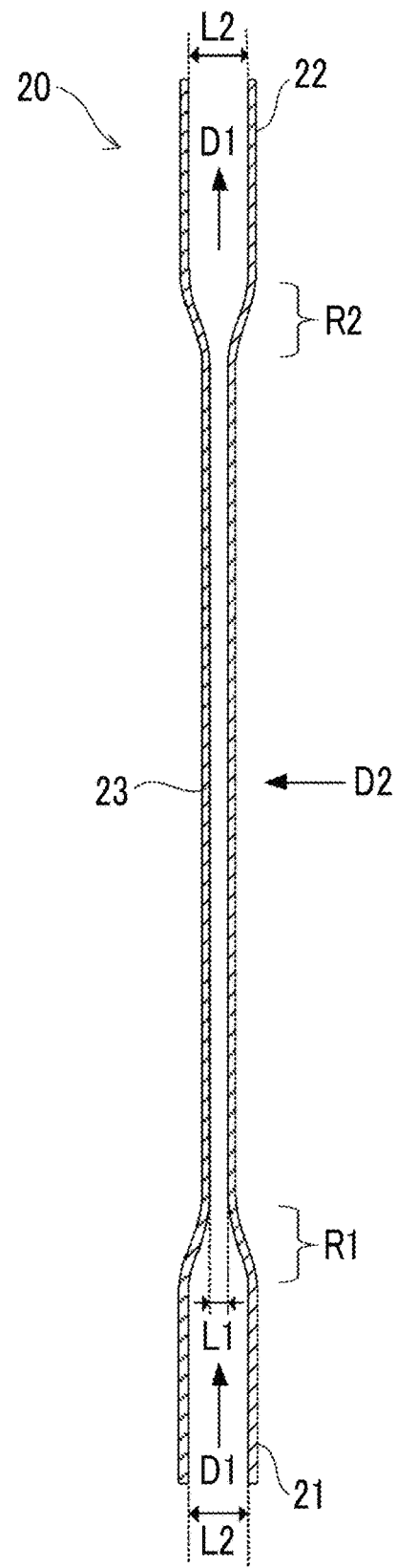
FIG. 2B is a cross-sectional view of the flow cell taken along line 2B-2B of FIG. 1.

FIG. 2A is a cross-sectional view of the flow cell 20 taken along line 2A-2A of FIG. 1, and FIG. 2B is a cross-sectional view of the flow cell 20 taken along line 2B-2B of FIG. 1. That is, each of FIGS. 2A and 2B shows a cross-section taken along a line parallel to the flow direction D1 of cell suspension that passes through the inside of the flow cell 20.

As shown in FIG. 2B, the thickness L1 of the flat flow passage 23 in the optical axis direction D2 (a direction parallel to the optical axis direction D2) is smaller than the thickness L2 of each of the inlet 21 and the outlet 22 in the same direction and is uniform. Here, the fact that the thickness L1 of the flat flow passage 23 in the optical axis direction is uniform means that the thickness L1 of the flat flow passage 23 is uniform within a range where an error is allowed. On the other hand, as shown in FIG. 2A, the length L3 of the flat flow passage 23 in a width direction D3 orthogonal to the flow direction D1 is longer than the length L2 of each of the inlet 21 and the outlet 22 in the same direction. Since the flat flow passage 23 has a configuration where two flat plates formed of members having light transmittance and a substantially constant thickness are disposed so that the principal surfaces of the flat plates are parallel to each other, the flat flow passage 23 has a flat shape where the thickness L1 of the flat flow passage 23 in the optical axis direction is significantly smaller than the length L3 of the flat flow passage 23 in the width direction D3.

In a case where the thickness L1 of the flat flow passage 23 is small, it is difficult for cells and the like, which pass through the inside of the flow cell 20, to overlap with each other and it is easy for the entire area of the flat flow passage 23 in the optical axis direction D2 to be in the range of the depth of focus of the imaging part 30. On the other hand, since the length L3 of the flat flow passage 23 in the width direction D3 needs to be increased in a case where the thickness L1 of the flat flow passage 23 is too small, the imaging field Q1 of view of the imaging part 30 needs to be increased according to this need. Further, as the cross-sectional area of the flow passage of the flow cell 20 in a direction crossing the flow direction D1 of cell suspension (hereinafter, referred to as a flow passage area) is reduced, the speed of the flow of cell suspension is increased. For this reason, the frame rate of the imaging part 30 needs to be increased. Considering this, the thickness L1 of the flat flow passage 23 in the optical axis direction D2 is preferably in the range of, for example, about 1.5 mm to 2.5 mm and is typically about 2 mm.

In terms of reducing damage to cells and the like passing through the flow cell 20, it is preferable that the maximum value of the speed of the flow of cell suspension passing through the flat flow passage 23 is substantially equal to the maximum value of the speed of the flow of cell suspension passing through the inlet 21 and the outlet 22. Here, the fact that the maximum value of the speed of the flow of cell suspension passing through the flat flow passage 23 is substantially equal to the maximum value of the speed of the flow of cell suspension passing through the inlet 21 and the outlet 22 means that a difference between the maximum value of the speed of the flow of cell suspension passing through the flat flow passage 23 and the maximum value of the speed of the flow of cell suspension passing through the inlet 21 and the outlet 22 is, for example, 10% or less. Further, making the flow passage areas of the inlet 21, the outlet 22, and the flat flow passage 23 be equal to each other is effective as a method of making the speed of the flow of cell suspension passing through the flow cell 20 uniform. Furthermore, it is preferable that the flow passage areas of the inlet 21, the outlet 22, and the flat flow passage 23 are 8 mm$^2$ or more. Since damage to cells is excessively increased in a case where the flow passage area is too small, it is possible to reduce damage to cells, which are passing through the flow cell 20, by setting the flow passage area to 8 mm$^2$ or more.

The imaging part 30 includes a plurality of imaging elements of which the imaging fields Q1 of view are set to the flat flow passage 23 of the flow cell 20. The entire area of the flat flow passage 23 in the width direction D3 orthogonal to the flow direction D1 of cell suspension, which passes through the inside of the flat flow passage 23, is included in the imaging field Q1 of view of the imaging part 30. The imaging part 30 continuously images cells and the like passing through the imaging field Q1 of view to generate a plurality of images.

The illumination part 40 is provided on one side of the flow cell 20 opposite to the imaging part 30, and irradiates the area of the flat flow passage 23, which corresponds to the imaging field Q1 of view, with illumination light.

Figure 3:
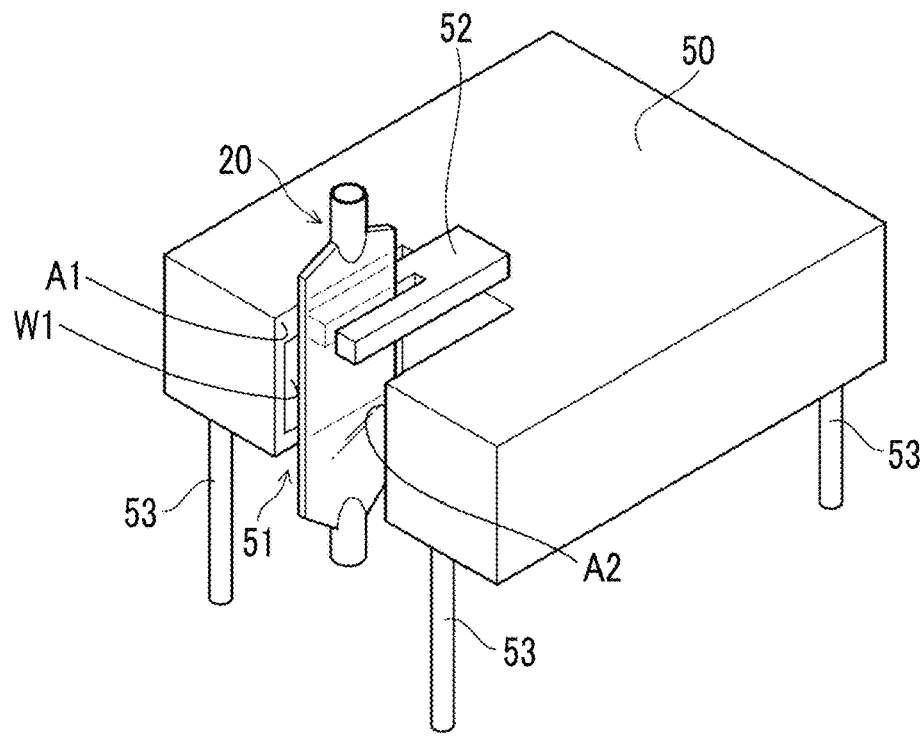
FIG. 3 is a perspective view showing an example of a configuration that is used to fix the relative positions of a flow cell, an imaging part, and an illumination part according to the embodiment of the technique of the disclosure.

FIG. 3 is a perspective view showing an example of a configuration that is used to fix the relative positions of the flow cells 20, the imaging part 30, and the illumination part 40. In an example shown in FIG. 3, the imaging part 30 and the illumination part 40 are housed in a housing 50. The housing 50 has the shape of a substantially rectangular parallelepiped, but a recessed portion 51 recessed toward the central portion of the housing 50 is formed at a part of the housing 50. At least a part of the flat flow passage 23 of the flow cell 20 is disposed in a space that is formed by the recessed portion 51 of the housing 50. The flow cell 20 is clamped by a clamper 52 fixed to the upper surface of the housing 50, so that the relative positions of the flow cell 20, the imaging part 30, and the illumination part 40 are fixed.

Window portions W1 and W2 (see FIG. 4) are provided on wall surfaces A1 and A2 that define the recessed portion 51 of the housing 50 and face each other, respectively. Illumination light, which is emitted from the illumination part 40, is transmitted through the window portion W2, the flow cell 20, and the window portion W1 and is incident on the imaging part 30. Four legs 53 are provided on the bottom of the housing 50. Since each of the legs 53 is extendable, the height of the housing 50 is variable.

Figure 4:
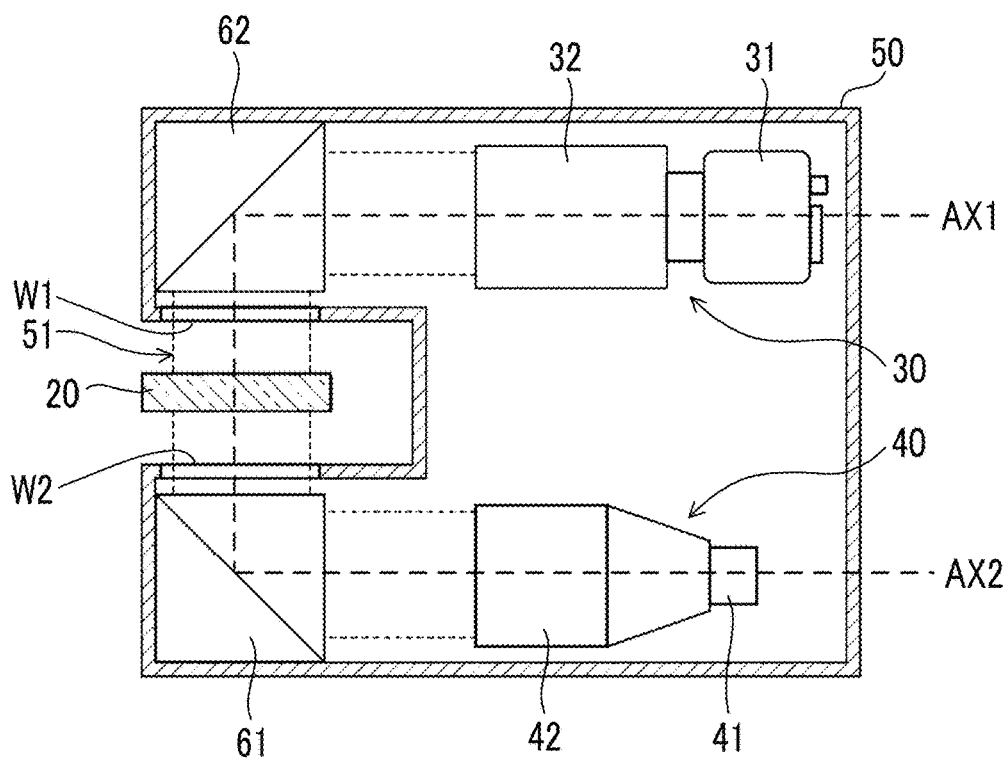
FIG. 4 is a diagram showing the configuration of the imaging part, the illumination part, and an optical system according to the embodiment of the technique of the disclosure that are housed in a housing.

FIG. 4 is a diagram showing the configuration of the imaging part 30, the illumination part 40, and an optical system that are housed in the housing 50.

The imaging part 30 includes an area sensor 31 where a plurality of imaging elements are arranged in the form of a matrix and a telecentric lens 32 that is provided on the light-incident side of the area sensor 31. That is, the telecentric lens 32 is provided between the flow cell 20 and the area sensor 31 on a path along a traveling direction of illumination light that is emitted from the illumination part 40. The area sensor 31 may have the form of, for example, a charge coupled device (CCD) camera or a complementary metal oxide semiconductor (CMOS) camera. It is preferable that the area sensor 31 has a frame rate for allowing each of cells and the like passing through the inside of the flow cell 20 to be imaged one or more times while cell suspension flows in the flow cell 20. The same cells and the like may be repeatedly included in the plurality of images that are acquired from the continuous imaging of the imaging part 30. In other words, each of the cells and the like may be imaged two or more times by the imaging part 30 while passing through the inside of the flow cell 20 one time. It is preferable that the maximum frame rate of the area sensor 31 is, for example, 100 fps or higher.

It is preferable that the size of one of the imaging elements of the area sensor 31 as an imaging resolution including lens magnification is smaller than several tens of μm that is the size of a single cell. For example, in a case where the magnification of the telecentric lens 32 is 1, the size of the imaging element may be about 5 μm. Further, the number of the imaging elements is determined according to lens magnification and the size of the imaging field Q1 of view. The number of the imaging elements is determined so that the entire area of the flat flow passage 23 in the width direction D3 orthogonal to the flow direction D1 of cell suspension passing through the inside of the flat flow passage 23 is included in the imaging field Q1 of view. The imaging part 30 comprises an area sensor 31 of which the number of imaging elements is, for example, 2000×1000. A case where the imaging part 30 includes the area sensor 31 has been exemplified in this embodiment, but a line sensor may be used instead of the area sensor 31.

Light, which arrives from the flow cell 20, is received by the area sensor 31 through the telecentric lens 32. The telecentric lens 32 is a lens of which a principal ray is parallel to the optical axis. Since the telecentric lens 32 is used, cells and the like passing through the inside of the flow cell 20 can be imaged as silhouette images. The reason for this is that the images of portions corresponding to the cells and the like are not formed on the imaging surface of the area sensor 31 since illumination light, which is applied to the flow cell 20 from the illumination part 40, is scattered by the cells and the like passing through the inside of the flow cell 20. Since the cells and the like are imaged as silhouette images as described above, the particle sizes and the number of the cells and the like can be very accurately measured. Further, the telecentric lens 32 has an advantage that the size of the image of an object to be imaged is scarcely changed even in a case where the object to be imaged moves in the optical axis direction. The particle sizes of the cells and the like passing through the inside of the flow cell 20 can be very accurately measured due to this advantage and the parallel flat surfaces that are formed by the flow cell 20.

At least the surface of the telecentric lens 32 close to the flow cell 20 has only to have telecentricity. That is, an object-side telecentric lens can be suitably used as the telecentric lens 32. A both-side telecentric lens, which has telecentricity on both the side thereof close to the flow cell 20 and the side thereof close to the area sensor 31, can also be used as the telecentric lens 32. The magnification of the telecentric lens 32 may be, for example, 1. Since the images acquired by the imaging part 30 are mainly used to count the number of cells and the like, the size of the imaging field of view is important. Since the imaging field of view is reduced in size in a case where the lens magnification is too high, the number of images to be acquired is increased and the load of image processing is increased. For this reason, it is not preferable that the lens magnification is too high. Since the particle size of a cell mass, which is a main object to be imaged by the imaging part 30, is about several tens to several hundreds of μm, the particle sizes and the number of cells and the like can be sufficiently measured using the images acquired by the imaging part 30 even though lens magnification is 1 in a case where the size of the imaging element is about 5 μm.

The illumination part 40 includes a light source 41 that emits illumination light for illuminating the imaging field Q1 of view of the imaging part 30, and a telecentric lens 42 that is disposed between the light source 41 and the flow cell 20. Every light emitting component, such as a light emitting diode (LED) lamp, an incandescent lamp, and a fluorescent lamp, can be used as the light source 41. Illumination light, which is emitted from the light source 41, is changed into collimated light by the telecentric lens 42. An optical axis AX2 of the telecentric lens 42 coincides with the optical axis AX1 of the telecentric lens 32 of the imaging part 30. Here, the fact that the optical axes of the telecentric lenses 32 and 42 coincide with each other means that the optical axes of the telecentric lenses 32 and 42 coincide with each other within a range where an error is allowed. Since collimated light parallel to the optical axis AX1 of the telecentric lens 32 of the imaging part 30 is used as illumination light as described above, the outlines of the cells and the like can be made sharp in the images acquired by the imaging part 30. Accordingly, the particle sizes of the cells and the like can be very accurately measured using the images acquired by the imaging part 30.

The traveling direction of illumination light emitted from the illumination part 40 is bent by an angle of 90° by a reflective prism 61, so that the illumination light is applied to the flow cell 20 disposed in the recessed portion 51 of the housing 50 and illuminates cells and the like contained in cell suspension flowing in the flow cell 20. The traveling direction of illumination light, is further bent by an angle of 90° by a reflective prism 62 and the images are incident on the imaging part 30. Since the traveling direction of light is bent using the reflective prisms 61 and 62 as described above, the imaging unit 10 can be made compact.

Since the illumination part 40 and the imaging part 30 are disposed so as to face each other as described above, illumination light, which is emitted from the illumination part 40 and corresponds to portions of the flow cell 20 where cells are not present, reaches the imaging part 30 just as it is and illumination light, which is emitted from the illumination part 40 and corresponds to portions of the flow cell 20 where cells are present, is irregularly reflected by the cells. Accordingly, since the illumination light corresponding to the portions of the flow cell 20 where cells are present is not transmitted to the imaging part 30, the portions of the flow cell 20 where cells are present are recorded as shadows. It is preferable that the illumination light emitted from the illumination part 40 is collimated light. Since the shadows obtained by the imaging part 30 are darker as the amount of diffuse components included in the illumination light is smaller, high detection accuracy can be obtained.

The operation of the imaging unit 10 will be described below. The imaging unit 10 is installed in a cell culture apparatus. The cell culture apparatus includes, for example, a culture vessel that is used to culture a cell, various treatment units that perform predetermined treatment on cell suspension, a flow passage that connects the culture vessel to the various treatment units, and a pump as liquid feed means. The flow cell 20 of the imaging unit 10 is inserted in the middle of the flow passage of the cell culture apparatus. It is preferable that the imaging unit 10 is installed in the middle of the flow passage through which all cells cultured in the cell culture apparatus pass. Accordingly, all the cells and the like cultured in the cell culture apparatus can be imaged by the imaging unit 10 and a plurality of images capturing all the cells and the like can be acquired.

Cell suspension, which flows in the flow passage of the cell culture apparatus, flows into the flow cell 20 from the inlet 21, passes through the flat flow passage 23, and flows to the outside of the flow cell 20 from the outlet 22. The imaging field Q1 of view of the imaging part 30 is set to an area of the flat flow passage 23, and the imaging part 30 continuously images the cells and the like moving in the flat flow passage 23 to generate a plurality of images. The entire area of the flat flow passage 23 in the width direction D3 orthogonal to the flow direction D1 of cell suspension passing through the inside of the flat flow passage 23 is included in the imaging field Q1 of view. Further, the imaging part 30 images the cells and the like at a frame rate that allows each of the cells and the like passing through the inside of the flow cell 20 to be imaged one or more times. Accordingly, the cells and the like, which are being cultured, are imaged without omission by the imaging part 30. The illumination part 40 irradiates the flow cell 20 with illumination light while the imaging part 30 is imaging the cells and the like.

Figure 5:
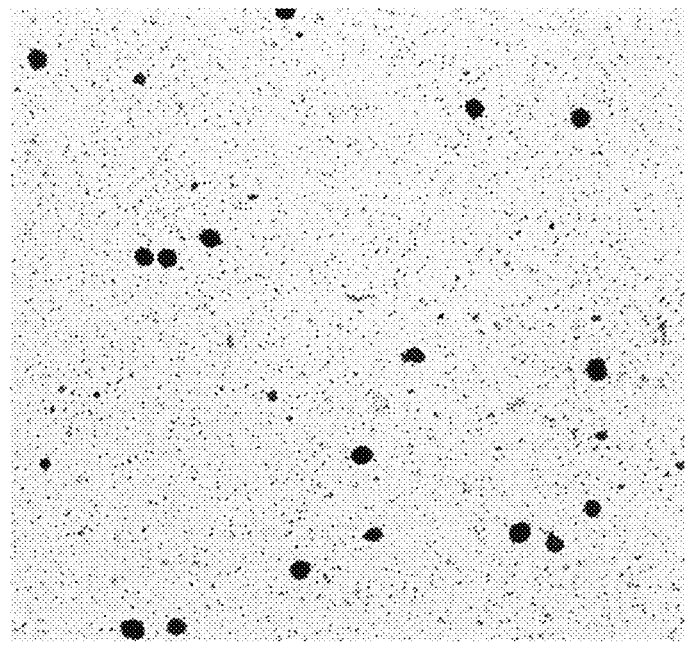
FIG. 5 is an example of an image that is acquired by the imaging unit according to the embodiment of the technique of the disclosure and captures cells and cell masses.

FIG. 5 is an example of an image that is acquired by the imaging unit 10 and captures cells and cell masses. According to the imaging unit 10 of this embodiment, cells and the like passing through the inside of the flow cell 20 can be imaged as silhouette images as shown in FIG. 5.

Figure 6:
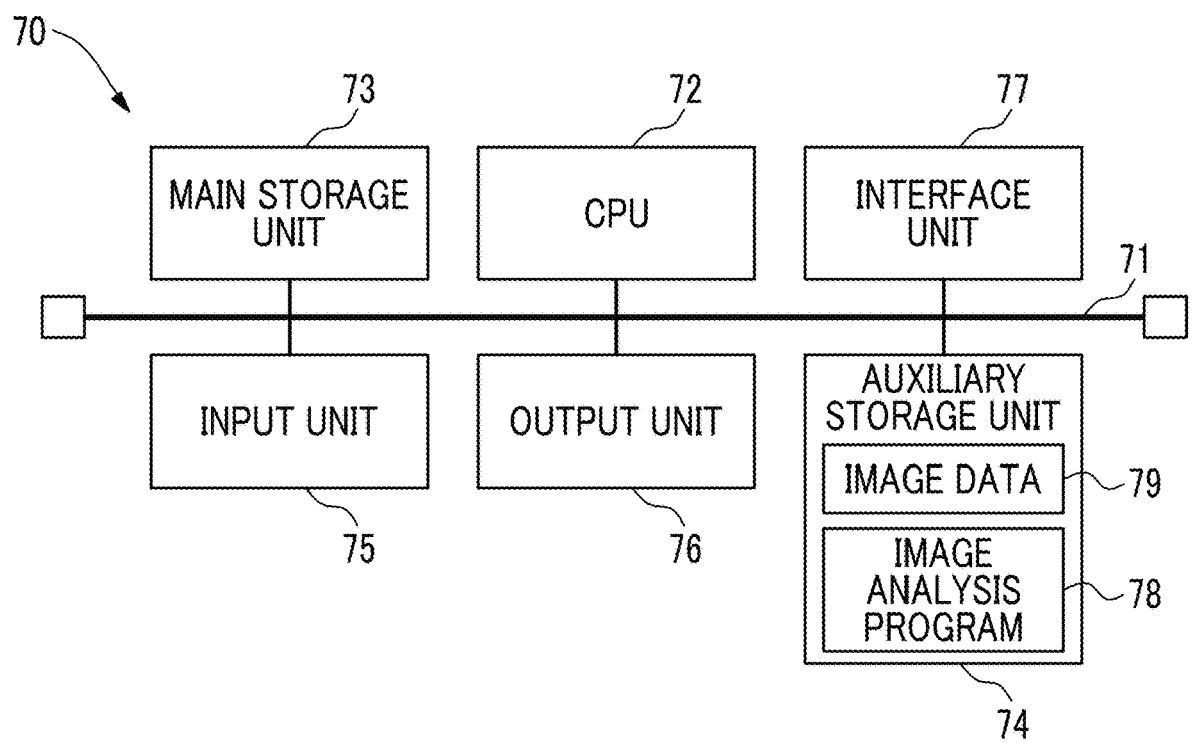
FIG. 6 is a block diagram showing an example of the configuration of an image analyzer according to an embodiment of the technique of the disclosure.

The imaging unit 10 according to this embodiment can further include an image analyzer 70 that analyzes the plurality of images acquired by the imaging part 30 to derive statistical data, such as particle size distribution, on cells and the like. The image analyzer 70 is an example of a derivation unit of the technique of the disclosure. FIG. 6 is a block diagram showing an example of the configuration of the image analyzer 70.

The image analyzer 70 is formed of a computer that includes a central processing unit (CPU) 72, a main storage unit 73, an auxiliary storage unit 74, an input unit 75, an output unit 76, and an interface unit 77 connected to each other through a bus 71.

In a case where the CPU 72 executes an image analysis program 78, the CPU 72 analyzes the plurality of images acquired by the imaging part 30 to derive statistical data, such as particle size distribution, on cells and the like. The main storage unit 73 has a storage area that is used to temporarily store a program being executed and data, and includes, for example, a random access memory (RAM). The input unit 75 includes, for example, a keyboard, a mouse, a tablet, and the like. The output unit 76 includes, for example, a display, a printer, and the like.

The auxiliary storage unit 74 is, for example, a non-volatile storage unit, such as a hard disk drive, and the image analysis program 78 and image data 79 representing the plurality of images acquired by the imaging part 30 are stored in the auxiliary storage unit 74. The plurality of images acquired by the imaging part 30 are received in the auxiliary storage unit 74 through the interface unit 77.

Figure 7:
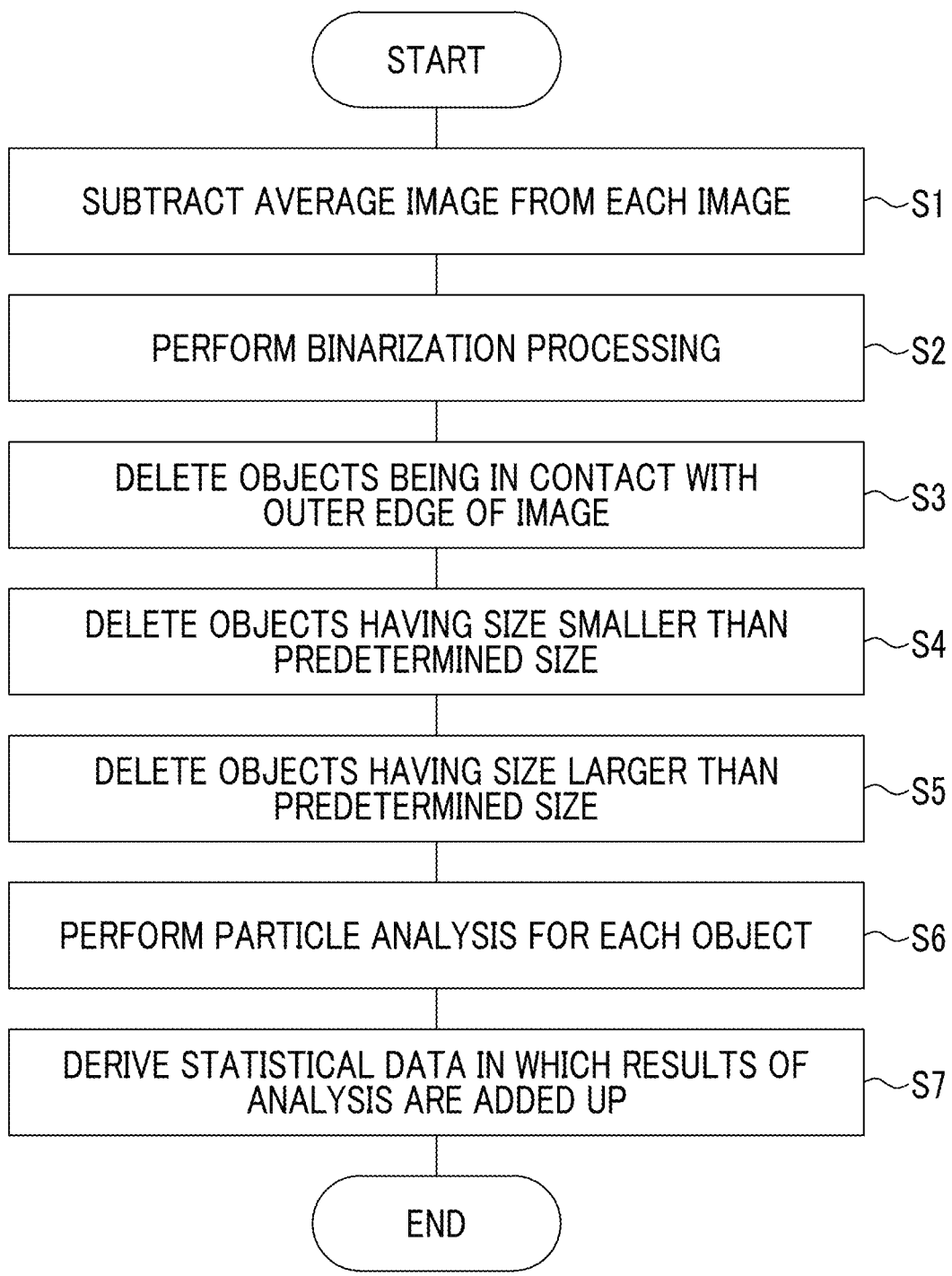
FIG. 7 is a flowchart showing the flow of processing to be performed in a case where a CPU of the image analyzer according to the embodiment of the technique of the disclosure executes an image analysis program.

FIG. 7 is a flowchart showing the flow of processing to be performed in a case where the CPU 72 executes the image analysis program 78.

In Step S1, the CPU 72 performs processing for subtracting an average image from each of a plurality of images that are acquired by the imaging part 30 and are represented by the image data 79 stored in the auxiliary storage unit 74. The dirt and scratch of the flow cell 20 are reflected on the all images in common. It is desirable that images common to all the images are subtracted as a background. The concentration distribution of the background can be acquired from the average image that is obtained in a case where the plurality of acquired images are averaged. The average image may be generated before the start of this routine.

In Step S2, the CPU 72 performs binarization processing on each of the plurality of images subjected to the processing of Step S1. Accordingly, the cells and the like are separated from the background. Further, each of the cells and the like included in each image is converted into one object of image processing.

In Step S3, the CPU 72 deletes the objects that are in contact with the outer edge of the image (the outer edge of the imaging field Q1 of view). That is, the cells and the like, which are in contact with the outer edge of the image (the outer edge of the imaging field Q1 of view) so that the entirety thereof is not shown, are excluded from an object to be subjected to image analysis. The reason for this is that the particle size of each of the cells and the like of which the entirety is not shown is measured to be smaller than an actual particle size. Even though the objects being in contact with the outer edge of the image (the outer edge of the imaging field Q1 of view) are deleted as described above, the influence of the deletion is reduced since the respective cells and the like are repeatedly imaged a plurality of times by the imaging part 30.

In Step S4, the CPU 72 performs processing for deleting objects having a size smaller than a predetermined size. In the culture where cell masses are not to be formed, the CPU 72 performs this processing to remove debris having a size smaller than the particle size of a cell. On the other hand, in the culture where cell masses are to be formed, the subsequent proliferation of cell masses having a particle size of, for example, 50 μm or less cannot be expected and such cell masses often become dead cells. Accordingly, the CPU 72 performs this processing to exclude such cell masses from an object to be subjected to image analysis.

In Step S5, the CPU 72 performs processing for deleting objects having a size larger than a predetermined size. Air bubbles, which have a particle size significantly larger than the particle size of a cell mass contained in a culture solution, may be mixed into a culture medium. Accordingly, it is preferable that an object, which is significantly large as compared to the size of a usual cell mass, is deleted to be excluded from an object to be subjected to image analysis.

In Step S6, the CPU 72 performs particle analysis for each object. Specifically, the CPU 72 derives the particle size and roundness of each object. The CPU 72 may derive a circle equivalent diameter as the particle size. The circle equivalent diameter is the diameter of a circle in a case where a region defined by the outline of an object is regarded as the circle having the same area as the region.

In Step S7, the CPU 72 derives data, in which results of the particle analysis performed in Step S6 are added up, as statistical data. The CPU 72 derives, for example, the number (particle size distribution) of cells and the like being in each predetermined particle size range, the number (density distribution) of cells and the like being in each predetermined particle size range per unit volume, the number (roundness distribution) of cells and the like being in each predetermined roundness range, and the total number of the cells, as statistical data. The derived statistical data are output to the output unit 76.

FIG. 8A is a diagram showing an example of an output form of the particle size distribution as statistical data that are derived by the image analyzer 70. The image analyzer 70 derives a value, which is obtained from the integration of the numbers of objects extracted from all the images acquired by the imaging part 30 for each grade of a particle size, as the integrated number Na of objects. In a case where the respective cells and the like are repeatedly imaged two or more times by the imaging part 30, the integrated number Na of objects is larger than the actual number of cells and the like (actual number). Accordingly, the image analyzer 70 converts the integrated number Na of objects into the actual number Nb as follows.

Since the inside dimensions of the flow cell 20 are already known, a volume v in the imaging field Q1 of view of the imaging part 30 is already known. The product t×v of the total number t of the images, which are used to derive the integrated number Na of objects, and the volume v in the imaging field Q1 of view is obtained as a total volume. In a case where the total amount (total volume) of cell suspension having passed through the inside of the flow cell 20 is denoted by M, the actual number Nb corresponding to the integrated number Na of objects belonging to the grade of a certain particle size is represented by the following equation (1).

$$Nb = Na \times \frac{M}{t \times v} \quad (1)$$

The image analyzer 70 outputs a table in which the integrated numbers Na of objects and the actual numbers Nb obtained as described above are expressed as a two-dimensional array to the output unit 76 as particle size distribution.

FIG. 8B is a diagram showing an example of an output form of roundness distribution as statistical data that are derived by the image analyzer 70. The image analyzer 70 derives a value, which is obtained from the integration of the numbers of objects extracted from all the images acquired by the imaging part 30 for each grade of roundness, as the integrated number Na of objects. The image analyzer 70 converts the integrated number Na of objects into the actual number Nb according to Equation (1). The image analyzer 70 outputs a table in which the integrated numbers Na of objects and the actual numbers Nb obtained as described above are expressed as a two-dimensional array to the output unit 76 as roundness distribution.

Further, the image analyzer 70 derives a result, which is obtained in a case where the number of objects per unit volume is obtained for each grade of a particle size, as the density distribution of cells and the like. The density distribution of cells and the like can be derived as follows. That is, since the inside dimensions of the flow cell 20 are already known, a volume v in the imaging field Q1 of view of the imaging part 30 is already known. The product t×v of the total number t of the images, which are used to derive particle size distribution, and the volume v in the imaging field Q1 of view is obtained as a total volume. In a case where the integrated number of objects integrated for each grade of a particle size is denoted by Na, the number (density) d of cells and the like, which belong to the grade of a certain particle size, per unit volume is represented by the following equation (2).

$$d = \frac{Na}{t \times v} \quad (2)$$

Furthermore, the image analyzer 70 derives the total number of single cells, which are included in the total amount (total volume) of cell suspension having passed through the flow cell 20, as follows. The number (density distribution) of cells and the like being in each predetermined particle size range per unit volume of cell suspension can be obtained from Equation (2). Moreover, since the average particle size of single cells is already known, the volume of the single cell in a case where each single cell is regarded as a spherical body can be obtained. Likewise, since the particle sizes of cell masses have been measured, the volume of each cell mass in a case where each cell mass is regarded as a spherical body can be obtained on the basis of the particle size. In a case where the volume of each cell mass is divided by the volume of a single cell, the number of single cells forming each cell mass can be obtained. The number Nc of single cells per unit volume of cell suspension can be obtained by this calculation. Then, as shown in the following equation (3), the product of the total amount (total volume) M of cell suspension having passed through the flow cell 20 and the number Nc of single cells per unit volume of cell suspension can be obtained as the total number Nx of single cells included in the total amount (total volume) of cell suspension having passed through the flow cell 20.

$$Nx = Nc \times M \quad (3)$$

As described above, the imaging unit 10 according to this embodiment acquires a plurality of images that capture cells and the like passing through the inside of the flow cell 20. Further, the imaging unit 10 performs image analysis for each of the plurality of images to derive the particle size and roundness of each of the cells and the like and to derive particle size distribution, density distribution, roundness distribution, and the total number of the cells as statistical data on the cells and the like.

According to a method of measuring cells and the like by the imaging unit 10 according to this embodiment, an act for collecting cells and the like is unnecessary. Accordingly, it is possible to avoid the risk of biological contamination and cells are not consumed. Further, since the cells and the like can be automatically measured, efforts and time can be significantly reduced as compared to a manual method in the related art.

Furthermore, since the imaging unit 10 is installed in the middle of the flow passage through which all cells cultured in the cell culture apparatus are to pass, all the cells cultured in the cell culture apparatus can be used as an object to be measured. Accordingly, measurement accuracy can be improved as compared to a measurement method in the related art that uses only some collected cells as an object to be measured.

Further, the flow cell 20 has a flat shape where the thickness L1 of the flow cell 20 in the optical axis direction D2 is significantly smaller than the length L3 of the flow cell 20 in the width direction D3. Accordingly, it is difficult for cells and the like, which pass through the inside of the flow cell 20, to overlap with each other and it is easy for the entire area of the flow cell 20 in the optical axis direction D2 to be in the range of the depth of focus of the imaging part 30. Therefore, an influence of a depth direction on the imaging of the imaging part 30 can be reduced. Furthermore, since the flow cell 20 is formed in a flat shape, more cells and the like can be made to be included in the imaging field Q1 of view of the imaging part 30. As a result, imaging and subsequent image analysis can be efficiently performed. Moreover, since the flow cell 20 has a configuration where two flat plates having a substantially constant thickness are disposed so that the principal surfaces of the flat plates are parallel to each other, the distortion of an image caused by the surface shape of the flow cell 20 is not generated.

Further, the entire area of the flow cell 20 in the width direction D3 is in the imaging field Q1 of view of the imaging part 30. Accordingly, since the imaging part 30 performs continuous imaging while cell suspension is introduced into the flow cell 20, all cells and the like contained in the cell suspension can be imaged regardless of the amount of the cell suspension.

Furthermore, since the imaging part 30 comprises the telecentric lens 32, the imaging part 30 can image cells and the like passing through the inside of the flow cell 20 as silhouette images. Since the cells and the like are imaged as silhouette images as described above, the particle sizes and the number of the cells and the like can be accurately measured. Moreover, since the telecentric lens 32 has an advantage that the size of the image of an object to be imaged is scarcely changed even in a case where the object to be imaged moves in the optical axis direction, the particle sizes of the cells and the like passing through the inside of the flow cell 20 can be very accurately measured.

Further, the imaging unit 10 according to this embodiment includes the illumination part 40 that includes the light source 41 and the telecentric lens 42. The illumination part 40 emits collimated light, which is substantially parallel to the optical axis of the telecentric lens 32 of the imaging part 30, as illumination light. Accordingly, since the outlines of the cells and the like can be made sharp in the images acquired by the imaging part 30, the particle sizes of the cells and the like can be accurately measured.

Figure 9:
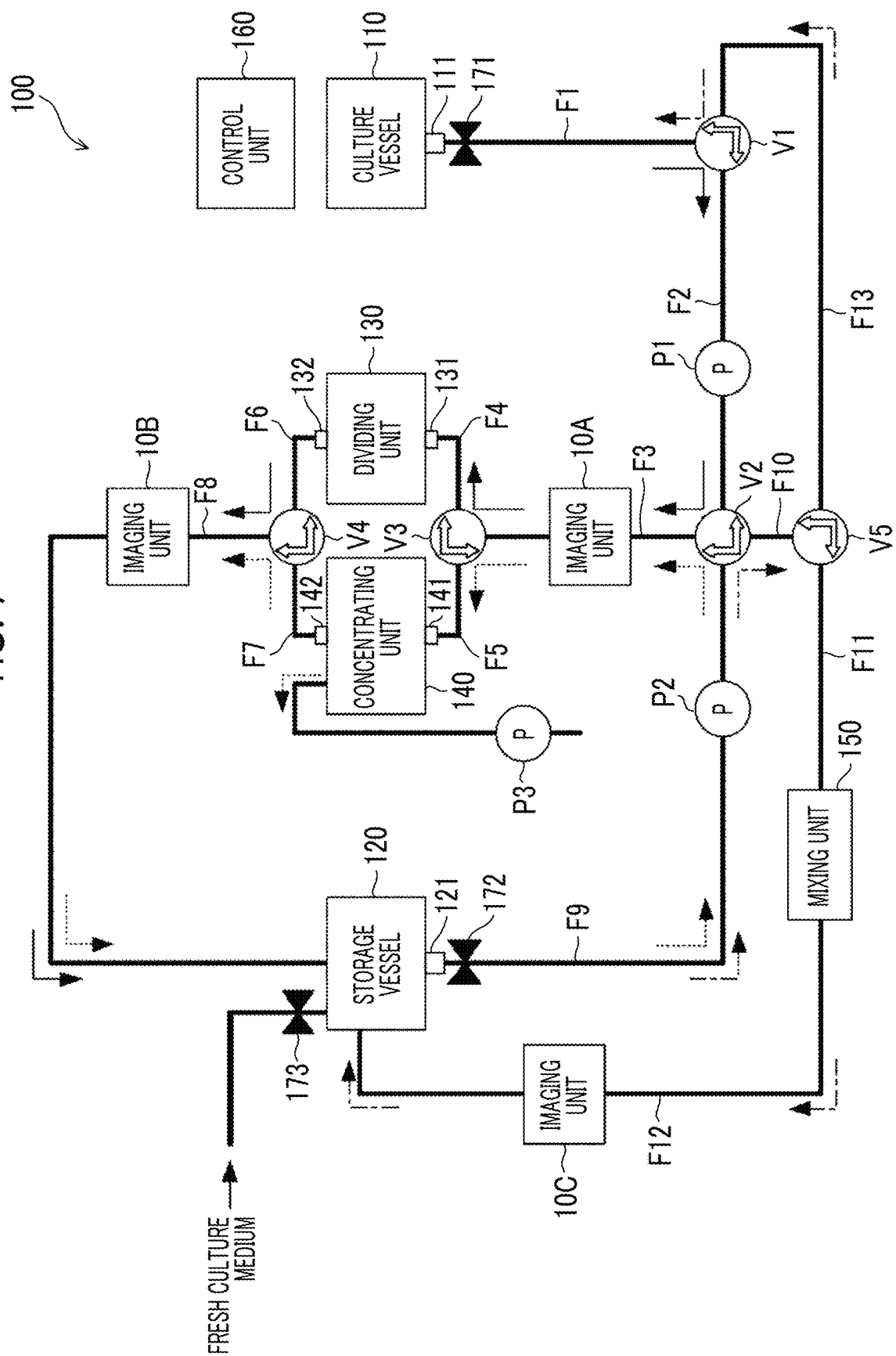
FIG. 9 is a diagram showing an example of the configuration of a cell culture apparatus according to an embodiment of the technique of the disclosure.

FIG. 9 is a diagram showing an example of the configuration of a cell culture apparatus 100 according to an embodiment of the technique of the disclosure comprising a plurality of imaging units 10. Three imaging units 10 of the cell culture apparatus 100 are written as imaging units 10A, 10B, and 10C, respectively, so as to be distinguished from each other.

The cell culture apparatus 100 includes a culture vessel 110 and a storage vessel 120 in which cell suspension is stored. Further, the cell culture apparatus 100 includes a dividing unit 130, a concentrating unit 140, and a mixing unit 150 as treatment units that perform predetermined treatment on cell suspension. Furthermore, the cell culture apparatus 100 includes flow passages F1 to F13 that are used to transfer cell suspension between the culture vessel 110, the storage vessel 120, the dividing unit 130, the concentrating unit 140, and the mixing unit 150. Moreover, the cell culture apparatus 100 includes pumps P1 and P2 that generate the flow of cell suspension and directional control valves V1 to V5 that control the flow direction of the cell suspension. Further, the cell culture apparatus 100 includes a control unit 160 that controls the drive of the pumps P1 and P2, the directional control valves V1 to V5, on/off valves 171 to 173 to be described later, and the imaging units 10A, 10B, and 10C. The pumps P1 and P2, the directional control valves V1 to V5, the on/off valves 171 to 173, and the imaging units 10A, 10B, and 10C can be connected to the control unit 160 by control wires, respectively, but the respective control wires are not shown in FIG. 9.

The culture vessel 110 is a vessel that stores cells and the like together with a culture medium and is used to culture the stored cells. The form of the culture vessel 110 is not particularly limited, and, for example, a vessel made of glass or stainless steel or a vessel made of plastic and having the form of a bag can be used. The culture vessel 110 can be housed in an incubator (not shown) of which the temperature is controlled in the range of, for example, 30° C. to 40° C. (preferably 37° C.) and $CO_2$ concentration is controlled in the range of 2% to 10% (preferably 5%) and which is sealed.

The on/off valve 171 is provided near a flow port 111 of the culture vessel 110 on the flow passage F1 connected to the culture vessel 110. The on/off valve 171 is controlled to be in an open state in a case where cell suspension is made to flow out of the culture vessel 110 and a case where cell suspension is made to flow into the culture vessel 110, and is controlled to be in a closed state in other cases. The on/off control of the on/off valve 171 is performed by the control unit 160.

The dividing unit 130 is a treatment unit that performs division treatment for dividing cell masses, which are formed due to the culture of cells in the culture vessel 110, into a plurality of cell masses having a smaller particle size. Since a plurality of single cells aggregate due to the culture of cells and form cell masses in the culture of pluripotent stem cells, the particle sizes of the cell masses are increased with the proliferation of cells. In a case where the particle sizes of cell masses are too large, there may be a problem that the cell masses adhere to and unite with each other and cells positioned at the central portions of the cell masses become necrotic. Accordingly, division treatment for dividing cell masses into a plurality of cell masses having a smaller particle size is necessary at an appropriate time during a culture period to prevent the particle sizes of cell masses from being too large.

The dividing unit 130 includes a mesh of which openings have a size smaller than the particle sizes of the cell masses. The cell masses are made to pass through the mesh, so that the cell masses are divided into a plurality of cell masses having a particle size corresponding to the size of each opening of the mesh. The dividing unit 130 includes an inlet 131 and an outlet 132, divides cell masses contained in cell suspension flowing in from the inlet 131, and makes the cell suspension having been subjected to treatment flow out of the outlet 132. Cell masses, which are divided by the dividing unit 130, are stored in the culture vessel 110, and a new culture cycle is started. Since a new culture cycle is started after the division treatment as described above, the division treatment can be grasped as subculture treatment.

Figure 10:
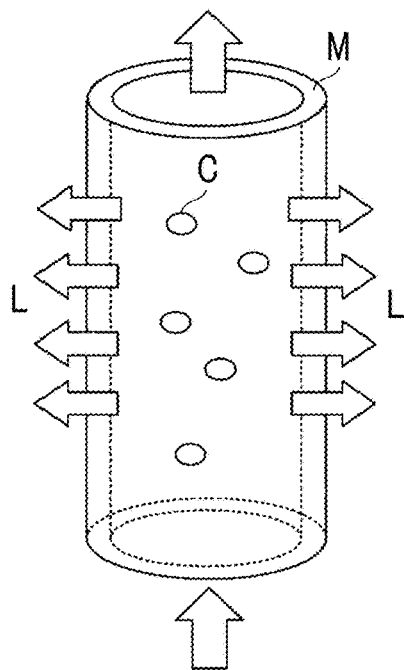
FIG. 10 is a perspective view showing an example of an aspect of filtration that is performed by a concentrating unit according to an embodiment of the technique of the disclosure.

The concentrating unit 140 is a treatment unit that performs concentration treatment for separating the culture medium contained in the cell suspension from cells and the like by a membrane to increase the concentration of the cells in the cell suspension. The concentrating unit 140 has the configuration of, for example, a tangential flow filter, and is adapted so that cell suspension flows along the surface of a filter membrane. FIG. 10 is a diagram showing an example of an aspect of filtration that is performed by the concentrating unit 140. The concentrating unit 140 includes a filter membrane 143 that is made of, for example, a hollow fiber. The concentrating unit 140 may have the configuration of a dead-end flow filter where the flow direction of cell suspension is a direction orthogonal to the surface of a filter membrane. The concentrating unit 140 includes an inlet 141 and an outlet 142, performs concentration treatment on the cell suspension flowing in from the inlet 141, and makes the cell suspension having been subjected to the treatment flow out of the outlet 142. The used culture medium, which has been transmitted through the filter membrane 143 of the concentrating unit 140 and contains debris, is discarded as waste liquid. A pump P3, which applies negative pressure, is connected to the filtration side of the concentrating unit 140.

The mixing unit 150 is a treatment unit that performs mixing treatment for mixing the concentrated cell suspension and a fresh culture medium, which is supplied from a culture medium supply unit (not shown), to make the density of cells contained in the culture medium uniform. It is preferable that the mixing unit 150 has a configuration as a static mixer not including a drive unit. For example, the mixing unit 150 can include a tubular body and a stirring element that is fixed and installed in the tubular body and forms a spiral flow passage in the tubular body. The mixing unit 150 may be adapted to rotationally drive stirring blades to stir and mix the concentrated cell suspension and a fresh culture medium.

The storage vessel 120 is a vessel that is used to primarily store cell suspension. The form of the storage vessel 120 is not particularly limited, and, for example, a vessel made of glass or stainless steel or a vessel made of plastic and having the form of a bag can be used.

The on/off valve 172 is provided near an outlet 121 of the storage vessel 120 on the flow passage F9 connected to the storage vessel 120. The on/off valve 172 is controlled to be in an open state in a case where cell suspension is made to flow out of the storage vessel 120, and is controlled to be in a closed state in other cases. The on/off control of the on/off valve 172 is performed by the control unit 160.

The flow passage F3 branches into the flow passage F4 connected to the inlet 131 of the dividing unit 130 and the flow passage F5 connected to the inlet 141 of the concentrating unit 140, and the directional control valve V3 is provided at an intersection of the flow passages F3, F4, and F5. Further, the flow passage F6 connected to the outlet 132 of the dividing unit 130 and the flow passage F7 connected to the outlet 142 of the concentrating unit 140 join the flow passage F8, and the directional control valve V4 is provided at an intersection of the flow passages F6, F7, and F8. The division treatment of the dividing unit 130 or the concentration treatment of the concentrating unit 140 can be selectively performed by the switching of the directional control valves V3 and V4.

The imaging unit 10A is provided in the middle of the flow passage F3 on the upstream side (inlet side) of the dividing unit 130 and the concentrating unit 140. That is, the flow cell 20 of the imaging unit 10A is inserted in the middle of the flow passage F3. The imaging unit 10B is provided in the middle of the flow passage F8 on the downstream side (outlet side) of the dividing unit 130 and the concentrating unit 140. That is, the flow cell 20 of the imaging unit 10B is inserted in the middle of the flow passage F8. The imaging unit 10C is provided in the middle of the flow passage F12 provided on the downstream side of the mixing unit 150. That is, the flow cell 20 of the imaging unit 10C is inserted in the middle of the flow passage F12.

The operation of each part of the cell culture apparatus 100 in a case where the division treatment is performed will be described below. The control unit 160 controls the directional control valves V1 to V4 to form a liquid feed route allowing the cell suspension, which is stored in the culture vessel 110, to reach the storage vessel 120 through the dividing unit 130. Then, the control unit 160 controls the on/off valve 171 to make the on/off valve 171 be in an open state, and activates the pump P1. Accordingly, the cell suspension stored in the culture vessel 110 flows into the dividing unit 130 through the flow passages F1, F2, F3, and F4.

The control unit 160 makes the imaging unit 10A start imaging at a timing when cell suspension reaches the flow cell 20 of the imaging unit 10A provided in the middle of the flow passage F3. A time lag between a point of time when liquid starts to be fed by the pump P1 and a point of time when the imaging of the imaging unit 10A is started can be estimated from the flow rate of liquid to be fed per unit time by the pump P1 and the volume of the flow passage between the pump P1 and the imaging unit 10A. While the cell suspension passes through the flow passage F3, cells and the like contained in the cell suspension are continuously imaged by the imaging unit 10A and a plurality of images are acquired. The imaging unit 10A derives statistical data on the cells and the like immediately before the division treatment on the basis of the plurality of acquired images. Since all the cells and the like stored in the culture vessel 110 pass through the flow cell 20 of the imaging unit 10A, all the cultured cells are reflected on the statistical data. The control unit 160 makes the imaging unit 10A end imaging at a timing when the end of the cell suspension has passed through the flow cell 20 of the imaging unit 10A. In this way, an operation for feeding liquid by the pump P1 and an imaging operation of the imaging unit 10A are interlocked with each other in the cell culture apparatus 100 according to this embodiment.

Cell masses contained in the cell suspension flowing into the dividing unit 130 are divided into a plurality of cell masses having a smaller particle size. The cell suspension having been subjected to the division treatment is stored in the storage vessel 120 through the flow passages F6 and F8.

The control unit 160 makes the imaging unit 10B start imaging at a timing when cell suspension reaches the flow cell 20 of the imaging unit 10B provided in the middle of the flow passage F8. While the cell suspension passes through the flow passage F8, cells and the like contained in the cell suspension are continuously imaged by the imaging unit 10B and a plurality of images are acquired. The imaging unit 10B derives statistical data on the cells and the like immediately after the division treatment on the basis of the plurality of acquired images. Since all the cells and the like stored in the culture vessel 110 pass through the flow cell 20 of the imaging unit 10B, all the cultured cells are reflected on the statistical data. The control unit 160 makes the imaging unit 10B end imaging at a timing when the end of the cell suspension has passed through the flow cell 20 of the imaging unit 10B.

In a case where the division treatment is completed, the control unit 160 controls the directional control valves V1, V2, and V5 to form a liquid feed route allowing the cell suspension, which is stored in the storage vessel 120, to reach the culture vessel 110 through the flow passages F9, F10, F13, and F1. Then, the control unit 160 controls the on/off valves 171 and 172 to make the on/off valves 171 and 172 be in an open state, and activates the pump P2. Accordingly, the cell suspension stored in the storage vessel 120 flows into the culture vessel 110 through the flow passages F9, F10, F13, and F1, and a new culture cycle is started in the culture vessel 110.

As described above, according to the cell culture apparatus 100 of this embodiment, statistical data on the cells and the like before and after the division treatment are acquired in a case where the division treatment of the dividing unit 130 is performed.

In the culture of cells, a culture medium degenerates due to metabolites and the like secreted from the cells. For this reason, culture medium-replacement treatment for replacing the culture medium, which is stored in the culture vessel 110, with a fresh culture medium is necessary at an appropriate time during a culture period. The culture medium-replacement treatment includes concentration treatment for separating the used culture medium contained in the cell suspension from cells and the like to increase the concentration of the cells in the cell suspension, and dilution/mixing treatment for adding a fresh culture medium to the concentrated cell suspension and then mixing the fresh culture medium and the concentrated cell suspension.

The operation of each part of the cell culture apparatus 100 in a case where the concentration treatment is performed will be described below. The control unit 160 controls the directional control valves V1 to V4 to form a liquid feed route allowing the cell suspension, which is stored in the culture vessel 110, to reach the storage vessel 120 through the concentrating unit 140. Then, the control unit 160 controls the on/off valve 171 to make the on/off valve 171 be in an open state, and activates the pump P1. Accordingly, the cell suspension stored in the culture vessel 110 flows into the concentrating unit 140 through the flow passages F1, F2, F3, and F5.

The control unit 160 makes the imaging unit 10A start imaging at a timing when cell suspension reaches the flow cell 20 of the imaging unit 10A provided in the middle of the flow passage F3. A time lag between a point of time when liquid starts to be fed by the pump P1 and a point of time when the imaging of the imaging unit 10A is started can be estimated from the flow rate of liquid to be fed per unit time by the pump P1 and the volume of the flow passage between the pump P1 and the imaging unit 10A. While the cell suspension passes through the flow passage F3, cells and the like contained in the cell suspension are continuously imaged by the imaging unit 10A and a plurality of images are acquired. The imaging unit 10A derives statistical data on the cells and the like immediately before the concentration treatment on the basis of the plurality of acquired images. Since all the cells and the like stored in the culture vessel 110 pass through the flow cell 20 of the imaging unit 10A, all the cultured cells are reflected on the statistical data. The control unit 160 makes the imaging unit 10A end imaging at a timing when the end of the cell suspension has passed through the flow cell 20 of the imaging unit 10A. In this way, an operation for feeding liquid by the pump P1 and an imaging operation of the imaging unit 10A are interlocked with each other in the cell culture apparatus 100 according to this embodiment.

The cell suspension flowing into the concentrating unit 140 is separated into a used culture medium and cells and the like by a membrane. The concentrated cell suspension is stored in the storage vessel 120 through the flow passages F6 and F8. On the other hand, the used culture medium, which has been transmitted through the filter membrane of the concentrating unit 140 and contains debris, is discarded as waste liquid.

The control unit 160 makes the imaging unit 10B start imaging at a timing when cell suspension reaches the flow cell 20 of the imaging unit 10B provided in the middle of the flow passage F8. While the cell suspension passes through the flow passage F8, cells and the like contained in the cell suspension are continuously imaged by the imaging unit 10B and a plurality of images are acquired. The imaging unit 10B derives statistical data on the cells and the like immediately after the concentration treatment on the basis of the plurality of acquired images. Since all the cells and the like stored in the culture vessel 110 pass through the flow cell 20 of the imaging unit 10B, all the cultured cells are reflected on the statistical data. The control unit 160 makes the imaging unit 10B end imaging at a timing when the end of the cell suspension has passed through the flow cell 20 of the imaging unit 10B.

Cell suspension may be circulated between the concentrating unit 140 and the storage vessel 120 to perform the concentration treatment a plurality of times until the concentration of the cell suspension reaches a desired concentration. In this case, the control unit 160 may determine the completion of the concentration treatment on the basis of the statistical data after the concentration treatment that is acquired by the imaging unit 10B.

Figure 11:
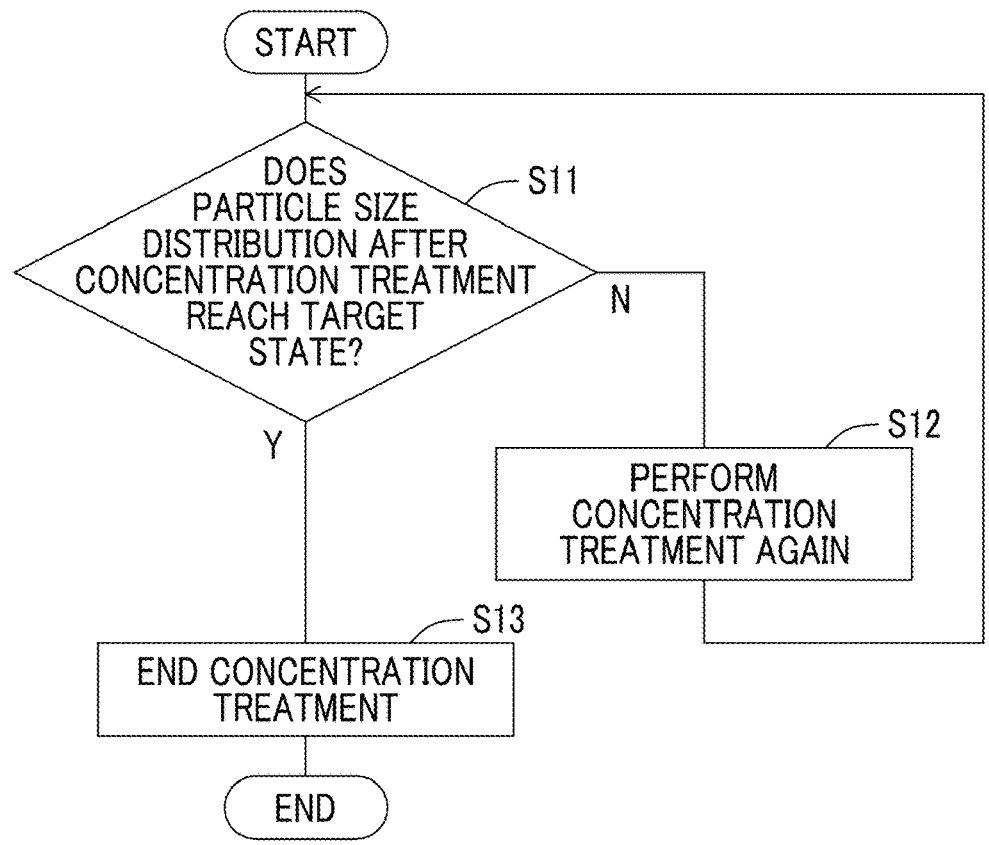
FIG. 11 is a flowchart showing an example of the determination of completion of concentration treatment that is performed in a control unit according to an embodiment of the technique of the disclosure.

FIG. 11 is a flowchart showing an example of the determination of completion of the concentration treatment that is performed in the control unit 160. In Step S11, the control unit 160 determines whether or not the number (particle size distribution) of cells and the like being in each predetermined particle size range after recent concentration treatment, which is derived by the imaging unit 10B, reaches a target state. In this step, the control unit 160 may determine whether or not the number (density distribution) of cells and the like per unit volume reaches a target state. If the control unit 160 determines that the particle size distribution or density distribution of cells and the like after the concentration treatment does not reach a target state, the control unit 160 makes processing proceed to Step S12.

In Step S12, the control unit 160 performs the concentration treatment again. That is, the control unit 160 controls the directional control valves V2, V3, and V4 to form a liquid feed route allowing the cell suspension, which is stored in the storage vessel 120, to return to the storage vessel 120 through the concentrating unit 140 again. Then, the control unit 160 controls the on/off valve 172 to make the on/off valve 172 be in an open state, and activates the pump P2. Accordingly, the cell suspension stored in the storage vessel 120 flows into the concentrating unit 140 through the flow passages F9, F3, and F5, and the concentration treatment is performed in the concentrating unit 140 again. Even in the second or later concentration treatment, statistical data on the cells and the like are acquired by each of the imaging units 10A and 10B. After that, processing returns to Step S11.

On the other hand, if the control unit 160 determines in Step S11 that the particle size distribution or density distribution of cells and the like after the concentration treatment reaches a target state, processing proceeds to Step S13. The control unit 160 determines in Step S13 that the concentration treatment is completed, and ends the concentration treatment.

As described above, according to the cell culture apparatus 100 of this embodiment, statistical data on the cells and the like before and after the concentration treatment are acquired in a case where the concentration treatment of the concentrating unit 140 is performed.

The operation of each part of the cell culture apparatus 100 in a case where the dilution/mixing treatment is performed will be described below. The control unit 160 controls the on/off valve 173 to make the on/off valve 173 be in an open state, so that a fresh culture medium is supplied to the storage vessel 120 in which the cell suspension having been subjected to the concentration treatment is stored. Accordingly, the cell suspension is diluted, so that the concentration of cells in the cell suspension is reduced.

Then, the control unit 160 controls the directional control valves V2 and V5 to form a liquid feed route allowing the cell suspension, which is stored in the storage vessel 120 and has been subjected to dilution treatment, to return to the storage vessel 120 through the mixing unit 150 again. After that, the control unit 160 controls the on/off valve 172 to make the on/off valve 172 be in an open state, and activates the pump P2. Accordingly, the cell suspension, which is stored in the storage vessel 120 and has been subjected to dilution treatment, flows into the mixing unit 150 through the flow passages F9, F10, and F11, and mixing treatment is performed in the mixing unit 150. Cell suspension having been subjected to the mixing treatment returns to the storage vessel 120 through the flow passage F12.

The control unit 160 makes the imaging unit 10C start imaging at a timing when cell suspension reaches the flow cell 20 of the imaging unit 10C provided in the middle of the flow passage F12. While the cell suspension passes through the flow passage F12, cells and the like contained in the cell suspension are continuously imaged by the imaging unit 10C and a plurality of images are acquired. The imaging unit 10C derives statistical data on the cells and the like immediately after the mixing treatment on the basis of the plurality of acquired images. Since all the cells and the like stored in the culture vessel 110 pass through the flow cell 20 of the imaging unit 10C, all the cultured cells are reflected on the statistical data. The control unit 160 makes the imaging unit 10C end imaging at a timing when the end of the cell suspension has passed through the flow cell 20 of the imaging unit 10C.

Cell suspension may be circulated between the mixing unit 150 and the storage vessel 120 to perform the mixing treatment a plurality of times until the mixed state of the cell suspension reaches a desired state. In this case, the control unit 160 may determine the completion of the mixing treatment on the basis of the statistical data on the cells and the like immediately after the mixing treatment that is acquired by the imaging unit 10C.

Figure 12:
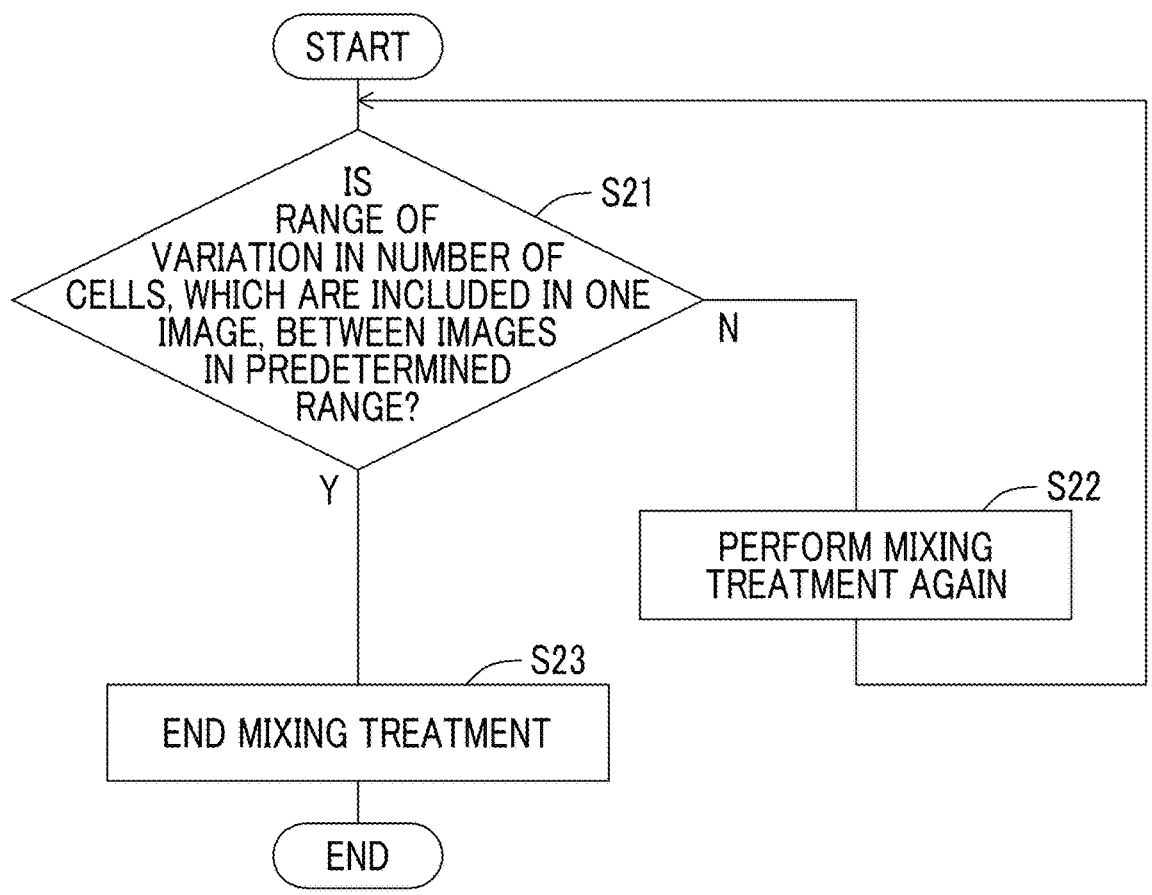
FIG. 12 is a flowchart showing an example of the determination of completion of mixing treatment that is performed in the control unit according to the embodiment of the technique of the disclosure.

FIG. 12 is a flowchart showing an example of the determination of completion of the mixing treatment that is performed in the control unit 160. In Step S21, the control unit 160 arranges the numbers of cells and the like, which are included in the respective images acquired by the imaging unit 10C, in order of the images, and acquires the range of variation in the number of cells and the like, which are included in one image, between the images. That is, the control unit 160 acquires the temporal change of the density of the cells and the like after the mixing treatment. The control unit 160 determines whether or not the range of variation in the number of cells and the like, which are included in one image, between the images is in a predetermined range. That is, it is determined in this determination processing whether or not the density of cells and the like in a culture medium is uniform. If the control unit 160 determines that the range of variation in the number of cells and the like, which are included in one image, between the images is not in the predetermined range, the control unit 160 makes processing proceed to Step S22.

In Step S22, the control unit 160 performs the mixing treatment again. That is, the control unit 160 controls the directional control valves V2 and V5 to form a liquid feed route allowing the cell suspension, which is stored in the storage vessel 120, to return to the storage vessel 120 through the mixing unit 150 again. Then, the control unit 160 controls the on/off valve 172 to make the on/off valve 172 be in an open state, and activates the pump P2. Accordingly, the cell suspension, which is stored in the storage vessel 120 and has been subjected to the dilution treatment, flows into the mixing unit 150 through the flow passages F9, F10, and F11, and the mixing treatment is performed in the mixing unit 150 again. Even in the second or later mixing treatment, statistical data are acquired by the imaging unit 10C. After that, processing returns to Step S21.

On the other hand, if the control unit 160 determines in Step S21 that the range of variation in the number of cells and the like, which are included in one image, between the images is in the predetermined range, processing proceeds to Step S23. The control unit 160 determines in Step S23 that the mixing treatment is completed, and ends the mixing treatment.

As described above, according to the cell culture apparatus 100 of this embodiment, statistical data on the cells and the like after the mixing treatment are acquired in a case where the mixing treatment of the mixing unit 150 is performed.

In a case where the culture medium-replacement treatment including the concentration treatment and the dilution/mixing treatment is completed, the control unit 160 controls the directional control valves V1, V2, and V5 to form a liquid feed route allowing the cell suspension, which is stored in the storage vessel 120, to reach the culture vessel 110 through the flow passages F9, F10, F13, and F1. Then, the control unit 160 controls the on/off valves 171 and 172 to make the on/off valves 171 and 172 be in an open state, and activates the pump P2. Accordingly, the cell suspension stored in the storage vessel 120 flows into the culture vessel 110 through the flow passages F9, F10, F13, and F1, and the culture of cells is continued in the culture vessel 110.

Figure 13:
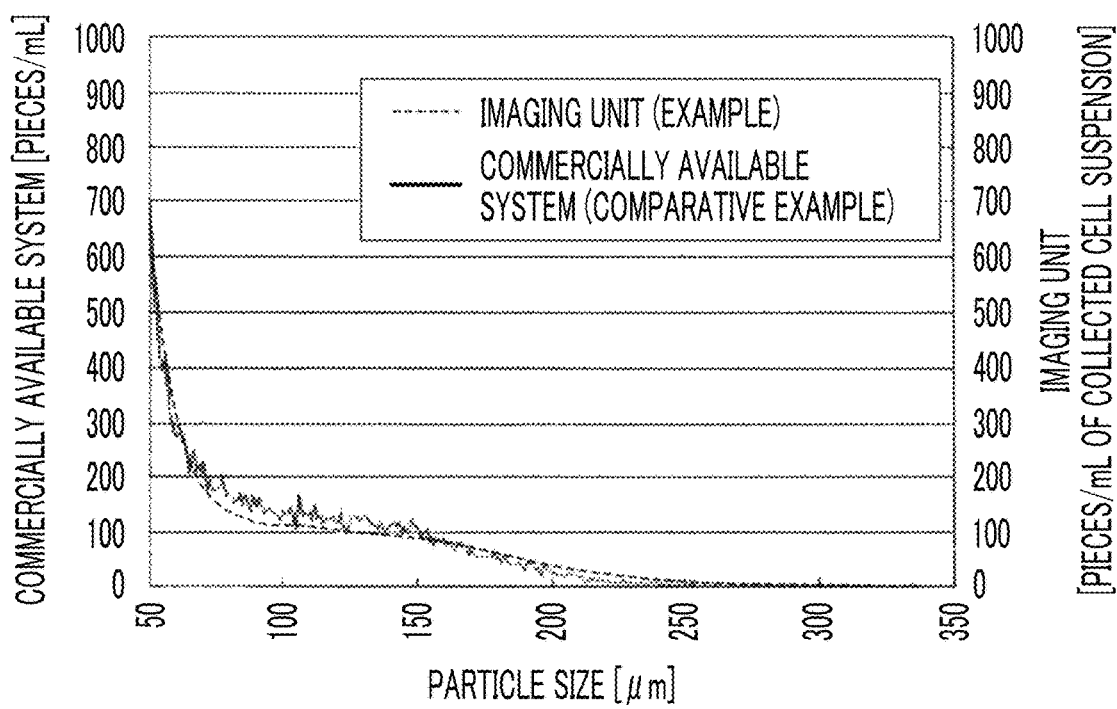
FIG. 13 is a graph showing the particle size distribution of cells and the like that is acquired using the imaging unit according to the embodiment of the technique of the disclosure and the particle size distribution of cells and the like that is acquired using a commercially available system.

FIG. 13 is a graph showing the particle size distribution of cells and the like that is acquired using the imaging unit 10 according to the embodiment of the technique of the disclosure and the particle size distribution of cells and the like that is acquired using a commercially available system. Multisizer 4e manufactured by Beckman Coulter, Inc. was used as the commercially available system. In FIG. 13, a horizontal axis represents the particle size of a cell or the like and a vertical axis represents the number of cells and the like per 1 mL of cell suspension. It is necessary to adjust the concentration of cells to a concentration, which is suitable for measurement, to perform accurate measurement by Multisizer 4e. For this reason, the cell suspension measured by the imaging unit 10 according to this embodiment was diluted 20 times, about 20 mL of the diluted cell suspension was sampled, and this sampled cell suspension was used for measurement using Multisizer 4e. Multisizer 4e converts the particle size distribution into the number of cells and the like per 1 mL of cell suspension, and outputs the number of cells and the like per 1 mL of cell suspension. In FIG. 13, a scale was reduced to a scale where the particle size distribution acquired using the imaging unit 10 according to this embodiment can be compared with the particle size distribution acquired using Multisizer 4e and was shown. A difference between the particle size distribution acquired using the imaging unit 10 according to this embodiment and the particle size distribution acquired using Multisizer 4e was about ±10%, and a result where both the particle size distribution acquired using the imaging unit 10 according to this embodiment and the particle size distribution acquired using Multisizer 4e substantially coincide with each other was obtained. As described above, according to the imaging unit 10 of this embodiment, it was confirmed that particle size distribution can be acquired with an accuracy equivalent to the accuracy of a commercially available system capable of acquiring highly accurate particle size distribution.

Figure 14A:
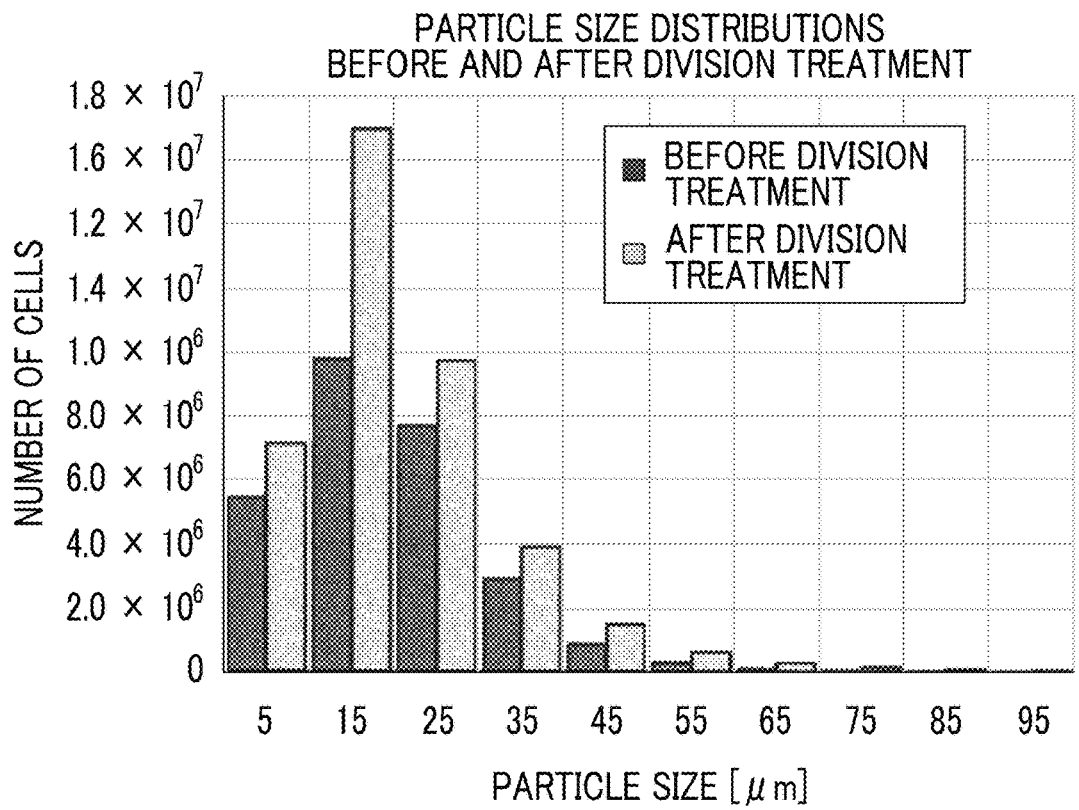
FIG. 14A is a graph showing the particle size distributions of cells and the like immediately before and after the division treatment of a dividing unit that are acquired using the imaging unit according to the embodiment of the technique of the disclosure.
Figure 14B:
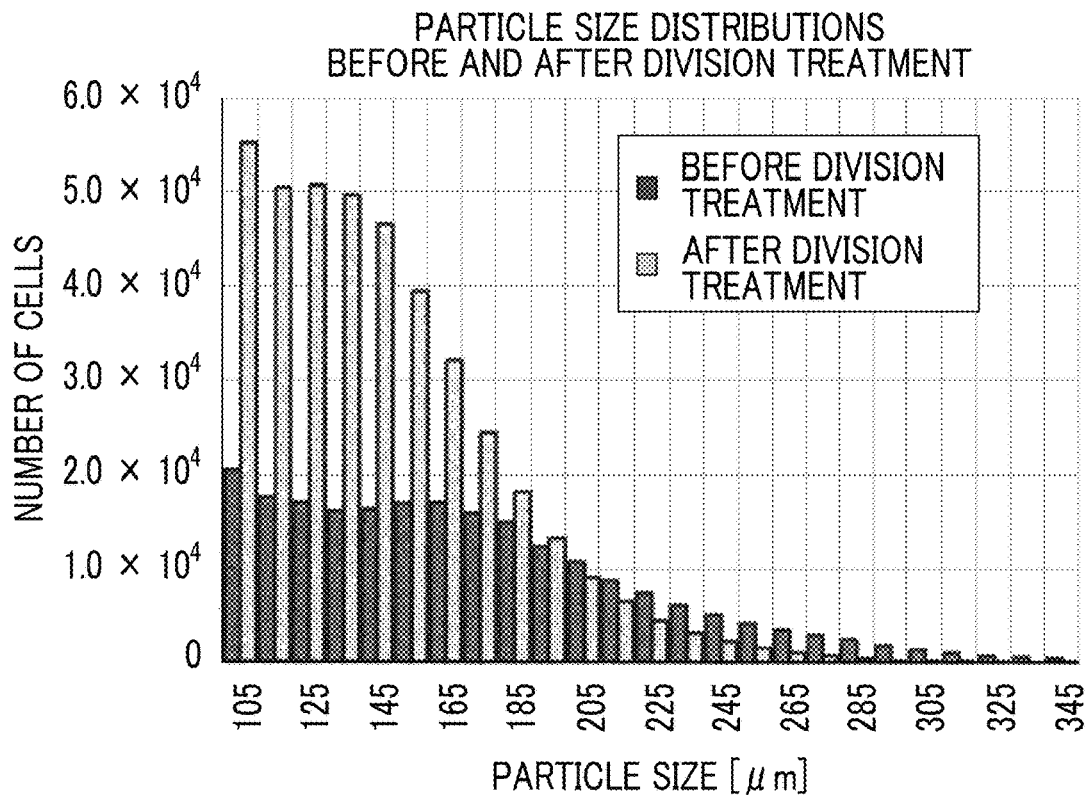
FIG. 14B is a graph showing the particle size distributions of cells and the like immediately before and after the division treatment of the dividing unit that are acquired using the imaging unit according to the embodiment of the technique of the disclosure.

FIGS. 14A and 14B are graphs showing the particle size distributions of cells and the like immediately before and after the division treatment of the dividing unit 130 that are acquired using the imaging units 10A and 10B provided in the cell culture apparatus 100 according to the embodiment of the technique of the disclosure, respectively. In FIGS. 14A and 14B, a horizontal axis represents the particle size of a cell or the like and a vertical axis represents the number of cells and the like. The particle size distribution of cells and the like immediately before the division treatment was acquired using the imaging unit 10A provided on the upstream side (inlet 131 side) of the dividing unit 130, and the particle size distribution of cells and the like immediately after the division treatment was acquired using the imaging unit 10B provided on the downstream side (outlet 132 side) of the dividing unit 130. It is found that the number of cell masses having a particle size exceeding 200 μm is reduced but the number of cell masses having a particle size smaller than 200 μm is increased since the division treatment is performed. Further, it is found that the total number of cell masses is increased since the division treatment is performed.

As described above, according to the cell culture apparatus 100 of this embodiment, the particle size distributions of cells and the like immediately before and after the division treatment of the dividing unit 130 can be acquired. It is possible to grasp how much the cell masses immediately before the division treatment have grown from the particle size distribution of cells and the like immediately before the division treatment. Further, it is possible to grasp the actual state of the division treatment from the shift of a peak of distribution in a case where the particle size distribution of cells and the like immediately before the division treatment is compared with the particle size distribution of cells and the like immediately after the division treatment. As described above, according to the cell culture apparatus 100 of this embodiment, it is possible to monitor whether or not the division treatment is performed as supposed since the actual state of the division treatment can be visualized.

The particle size distribution of cell masses after the division treatment depends on the speed of the flow of cell masses in a case where the cell masses pass through the mesh of the dividing unit 130. Accordingly, the speed of the flow of cell masses in a case where the cell masses pass through the mesh may be determined on the basis of the particle size distribution of cell masses after the division treatment. For example, a correlation between the speed of the flow and particle size distribution may be determined in advance, and the speed of the flow may be determined using this correlation so that the particle size distribution of cell masses after the division treatment becomes desired particle size distribution.

Figure 15A:
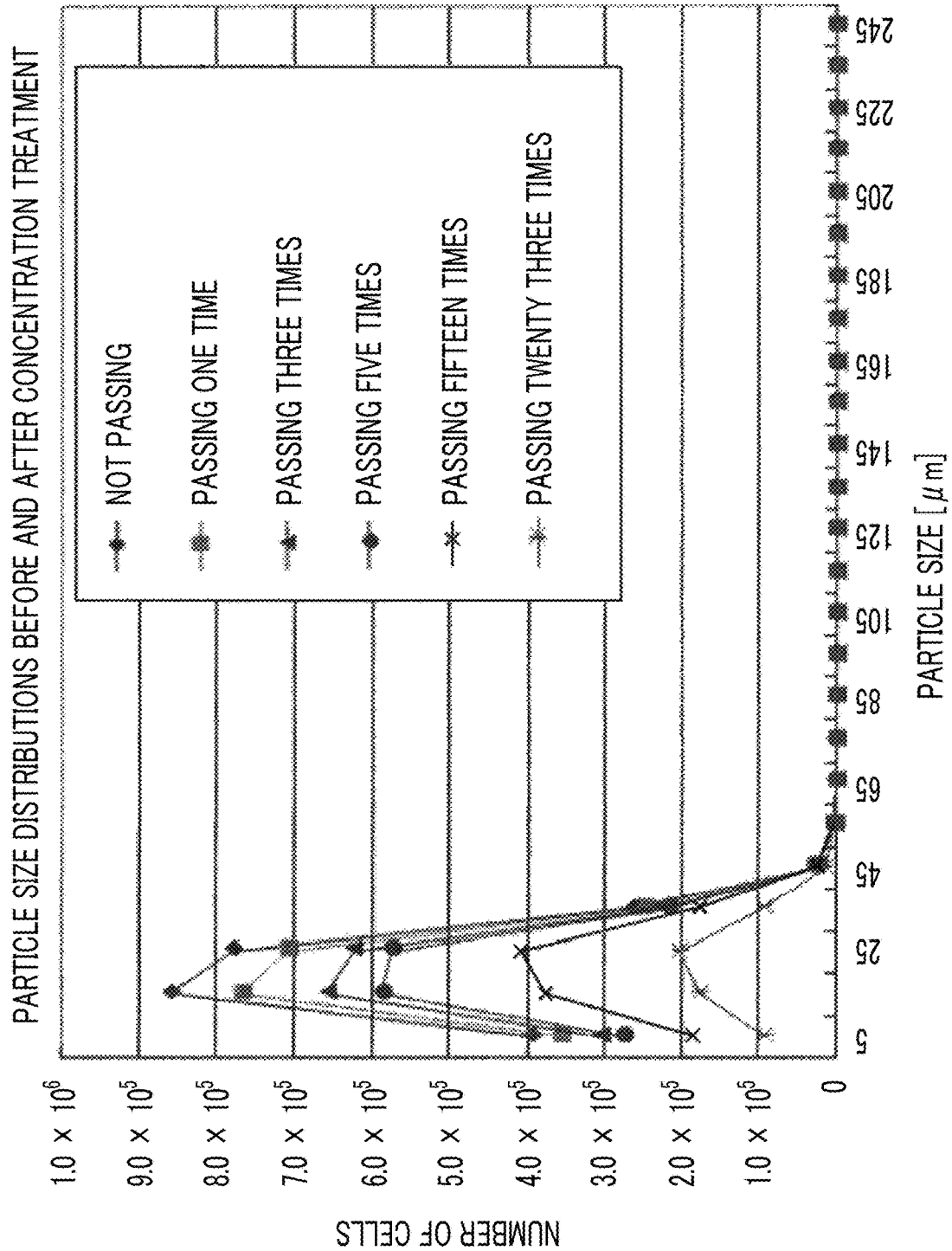
FIG. 15A is a graph showing the particle size distribution of cells and the like before the concentration treatment of the concentrating unit and the particle size distribution of cells and the like after the concentration treatment of the concentrating unit that are acquired using the imaging unit according to the embodiment of the technique of the disclosure.
Figure 15B:
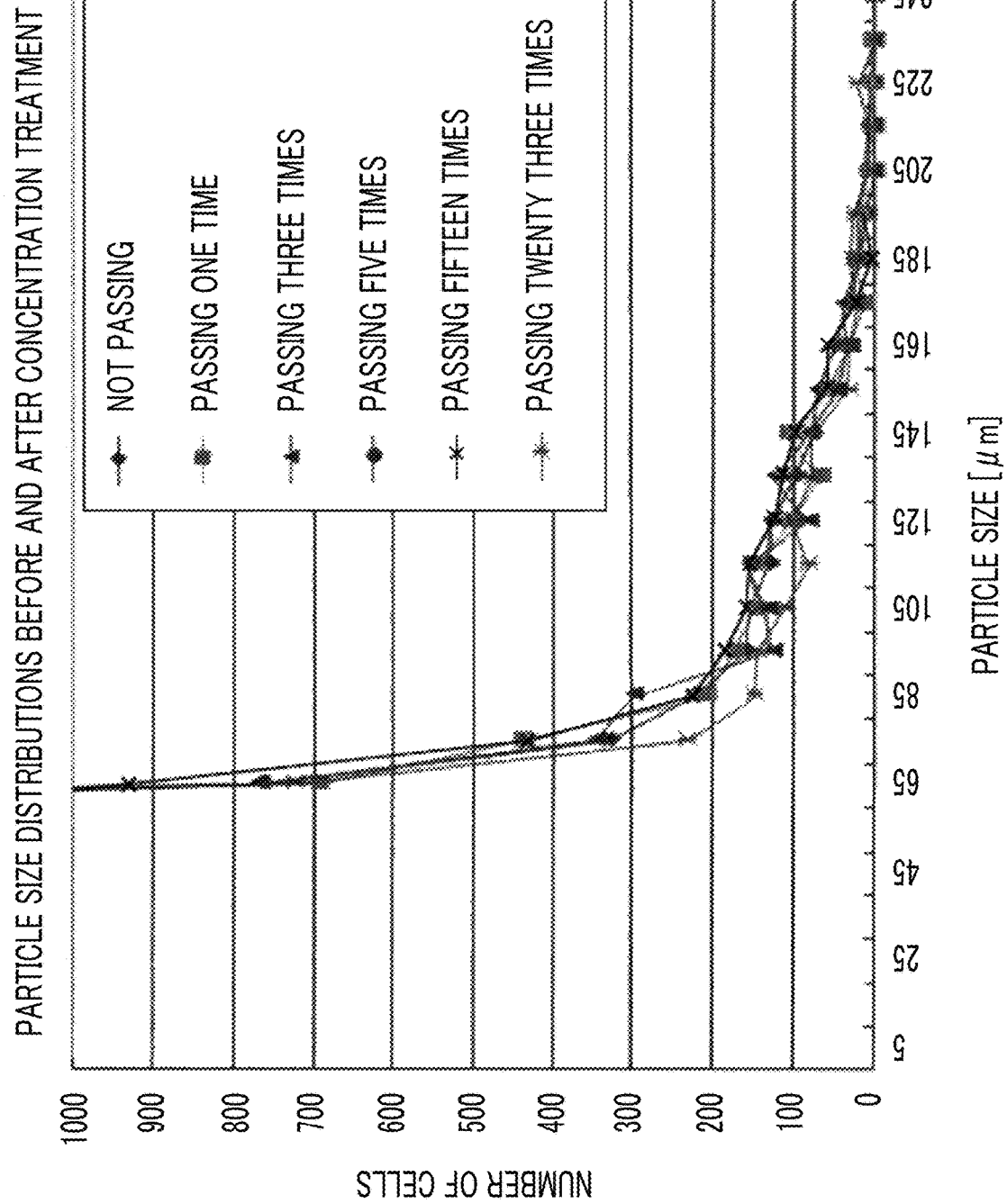
FIG. 15B is a graph showing the particle size distribution of cells and the like before the concentration treatment of the concentrating unit and the particle size distribution of cells and the like after the concentration treatment of the concentrating unit that are acquired using the imaging unit according to the embodiment of the technique of the disclosure.

FIGS. 15A and 15B are graphs showing the particle size distribution of cells and the like before the concentration treatment of the concentrating unit 140 and the particle size distributions of cells and the like after the concentration treatment of the concentrating unit 140 is performed one time, three times, five times, fifteen times, and twenty three times, which are acquired using the imaging units 10A and 10B. In FIGS. 15A and 15B, a horizontal axis represents the particle size of a cell or the like and a vertical axis represents the number of cells and the like. FIG. 15B is a graph showing the same measurement results as those of FIG. 15A in a state where a scale on the vertical axis is enlarged. The particle size distribution of cells and the like before the concentration treatment (in a case where the number of times of the concentration treatment is 0) was acquired using the imaging unit 10A provided on the upstream side (inlet 141 side) of the concentrating unit 140, and the particle size distribution of cells and the like after the concentration treatment was acquired using the imaging unit 10B provided on the downstream side (outlet 142 side) of the concentrating unit 140. The speed of the flow of cell suspension (the speed of the flow of the main stream) flowing on the supply side of a filter membrane of the concentrating unit 140 was set to 120 mL/min, and the speed of the flow of waste liquid flowing on the filtration side of the filter membrane of the concentrating unit 140 was set to 5 mL/min. It is found that the number of cells and the like having a particle size of 50 μm or less is reduced but the number of cells and the like having a particle size of 65 μm or more is scarcely changed whenever the number of times of the concentration treatment is increased as shown in FIG. 15A. That is, it could be confirmed that concentration treatment was appropriately performed in the concentrating unit 140.

As described above, according to the cell culture apparatus 100 of this embodiment, the particle size distributions of cells or the like before and after the concentration treatment of the concentrating unit 140 can be acquired. Further, it is possible to grasp a change in the particle size distribution of cells or the like in a case where the concentration treatment is performed a plurality of times. As described above, according to the cell culture apparatus 100 of this embodiment, it is possible to monitor whether or not the concentration treatment is performed as supposed since the actual state of the concentration treatment can be visualized. For example, in a case where the number of particles having a relatively small particle size after the concentration treatment significantly exceeds a target value, it is possible to deduce that suction pressure on the filtration side is low or the clogging of a filter is caused. Furthermore, in a case where the number of particles having a relatively large particle size starts to be reduced in the middle of the concentration treatment, it is possible to deduce that the clogging of a filter is caused, suction pressure to the filtration side rises at a part of a filter, and particles are crushed and flow out to the filtration side. In this case, a measure, such as the change of a suction pressure condition or the replacement of a filter, can be quickly taken.

Further, in a case where the concentration treatment is performed a plurality of times, the control unit may determine that the concentration treatment is completed when the particle size distribution or density distribution of cells and the like after the concentration treatment of the concentrating unit 140 reaches a target state. That is, the particle size distribution after the concentration treatment may be used to determine the completion of the concentration treatment as shown in FIG. 11.

Figure 16:
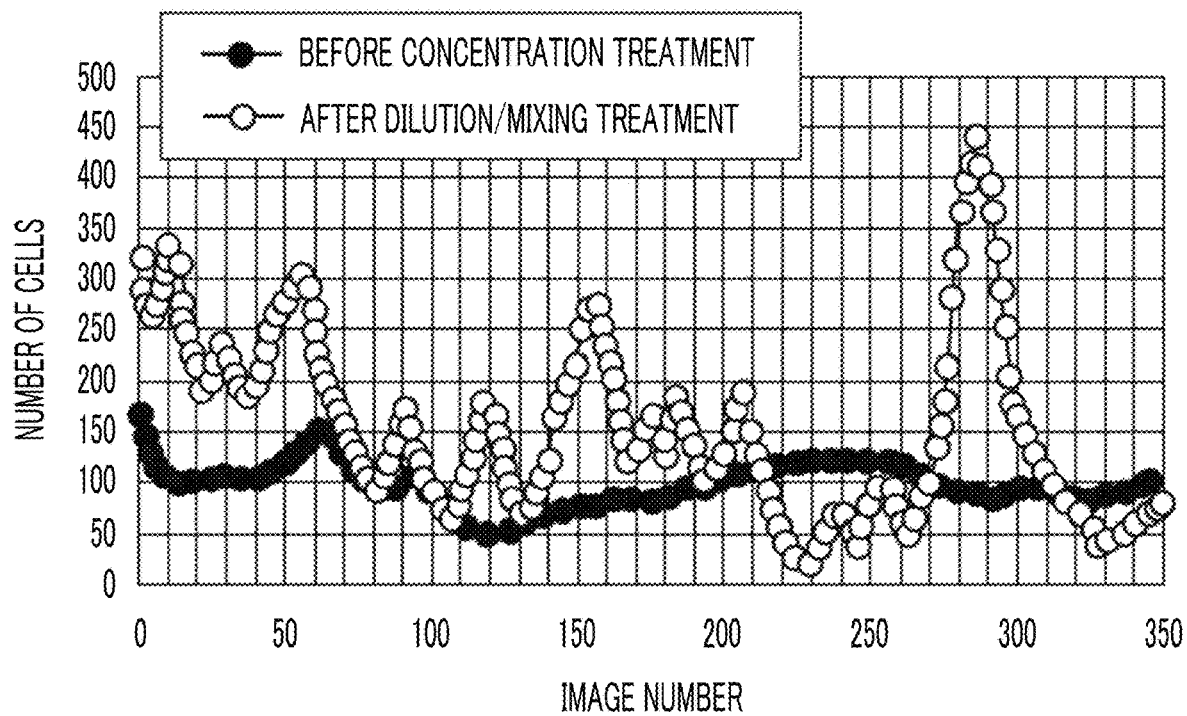
FIG. 16 is a graph showing a result where the numbers of cells and the like included in the respective acquired images are arranged in order of the images in a case where cell suspension flowing in a flow passage provided on the downstream side of a mixing unit according to an embodiment of the technique of the disclosure is continuously imaged by the imaging unit.

FIG. 16 is a graph showing a result where the numbers of cells or the like included in the respective acquired images are arranged in order of the images in a case where cell suspension flowing in the flow passage F12 provided on the downstream side of the mixing unit 150 is continuously imaged by the imaging unit 10C. That is, the graph of FIG. 16 shows the uniformity of the density of cells or the like flowing in the flow passage F12. In other words, FIG. 16 shows a state where the cells or the like and the culture medium are mixed. Further, FIG. 16 also shows a result where the numbers of cells or the like included in the respective acquired images are arranged in order of the images in a case where cell suspension flowing in the flow passage F3 provided on the upstream side of the concentrating unit 140 is continuously imaged by the imaging unit 10A. It is found that the density of cells or the like passing through the flow passage F12 provided on the downstream side of the mixing unit 150 is significantly changed as shown in FIG. 16. In a case where the cells and the like and the culture medium are uniformly mixed by the mixing treatment of the mixing unit 150, it is thought that the numbers of cells and the like included in the respective images are substantially the same between the images. That is, it can be found from the results shown in FIG. 16 that there is room for improvement of the mixing treatment of the mixing unit 150 since the density of the cells and the like contained in the culture medium is not uniform.

As described above, according to the cell culture apparatus 100 of this embodiment, it is possible to grasp the mixed state of the culture medium and the cells and the like after the mixing treatment of the mixing unit 150. That is, it is possible to grasp the actual state of the mixing treatment and to visualize the results of the mixing treatment. Accordingly, it is possible to monitor whether or not the mixing treatment is performed as supposed. For example, in a case where the density of cells and the like passing through the flow passage F12 provided on the downstream side of the mixing unit 150 is significantly changed as described above, a measure, such as the change of the speed of the flow when the cells and the like pass through the mixing unit 150, can be quickly taken.

Further, in a case where the mixing treatment is performed a plurality of times, the control unit may determine that the mixing treatment is completed when the temporal change of the density of cells and the like after the mixing treatment of the mixing unit 150 reaches a target state. That is, the temporal change of the number of cells and the like included in one image may be used to determine the completion of the mixing treatment as shown in FIG. 12.

Further, according to the cell culture apparatus 100 of this embodiment, it is possible to grasp the concentration of cell suspension after the dilution treatment by deriving the density distribution of the cells and the like on the basis of the plurality of images that are acquired by the imaging unit 10C.

According to the cell culture apparatus 100 of this embodiment, it is also possible to quantitatively grasp whether or not culture is smoothly performed. Examples of a direct index, which is used to confirm whether or not culture is smoothly performed, include the number of cell masses that are being cultured and the particle size of each of the cell masses. The division treatment (subculture treatment) of the dividing unit 130 is a process for increasing the number of cell masses, but all the increased cell masses cannot survive since stress is applied to cells at the time of division. Some of the increased cell masses may become dead cells and be decomposed.

In the culture of cells using the cell culture apparatus 100 according to this embodiment, the division treatment (subculture treatment) of the dividing unit 130 is performed for every predetermined period (for example, every five days). Further, the particle size distribution of cell masses immediately before the previous division treatment (subculture treatment) and the particle size distribution of cell masses immediately before the present division treatment (subculture treatment) are acquired and both the particle size distributions are compared with each other. Accordingly, it is possible to grasp the increment of the number of cell masses that is substantially increased by subculture. The particle size distribution of cell masses immediately before the division treatment can be acquired on the basis of the plurality of images that are acquired by the imaging unit 10A. Furthermore, the data on the particle size distribution of cell masses immediately before the division treatment are accumulated in each culture cycle, so that it is possible to determine whether or not culture is more smoothly performed than the average result of the past culture.

Further, it is possible to grasp how much the cell masses have grown during one cycle period of culture from the shift amount of a peak of particle size distribution in a case where the particle size distribution of cells and the like immediately after the previous division treatment (subculture treatment) is compared with the particle size distribution of cells and the like immediately before the present division treatment (subculture treatment). In a case where this data is accumulated for every batch of culture, a causal relationship between the particle size after the division treatment (subculture treatment) and the subsequent proliferation of cells can be obtained. That is, it is possible to obtain the particle size of each cell mass after the division treatment that allows the proliferation of cells after the division treatment to be most facilitated. Since this result can be fed back to the treatment condition of the division treatment, this result becomes means effective in determining more preferable treatment condition. The particle size distribution of cells and the like immediately after the division treatment (subculture treatment) can be acquired on the basis of the plurality of images that are acquired by the imaging unit 10B. The particle size distribution of cells and the like immediately before the division treatment (subculture treatment) can be acquired on the basis of the plurality of images that are acquired by the imaging unit 10A.

Figure 17A:
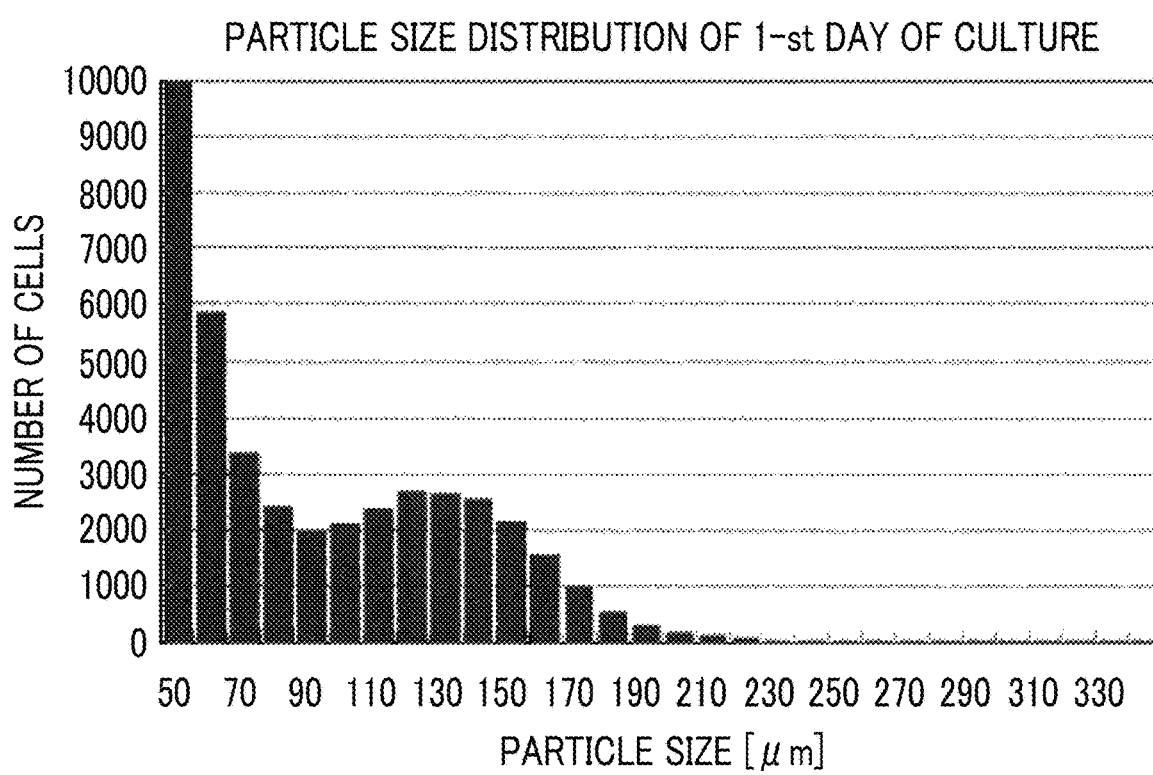
FIG. 17A is a graph showing the particle size distribution of cells and the like that is acquired at a different timing during one cycle period of the culture performed by the cell culture apparatus according to the embodiment of the technique of the disclosure.
Figure 17B:
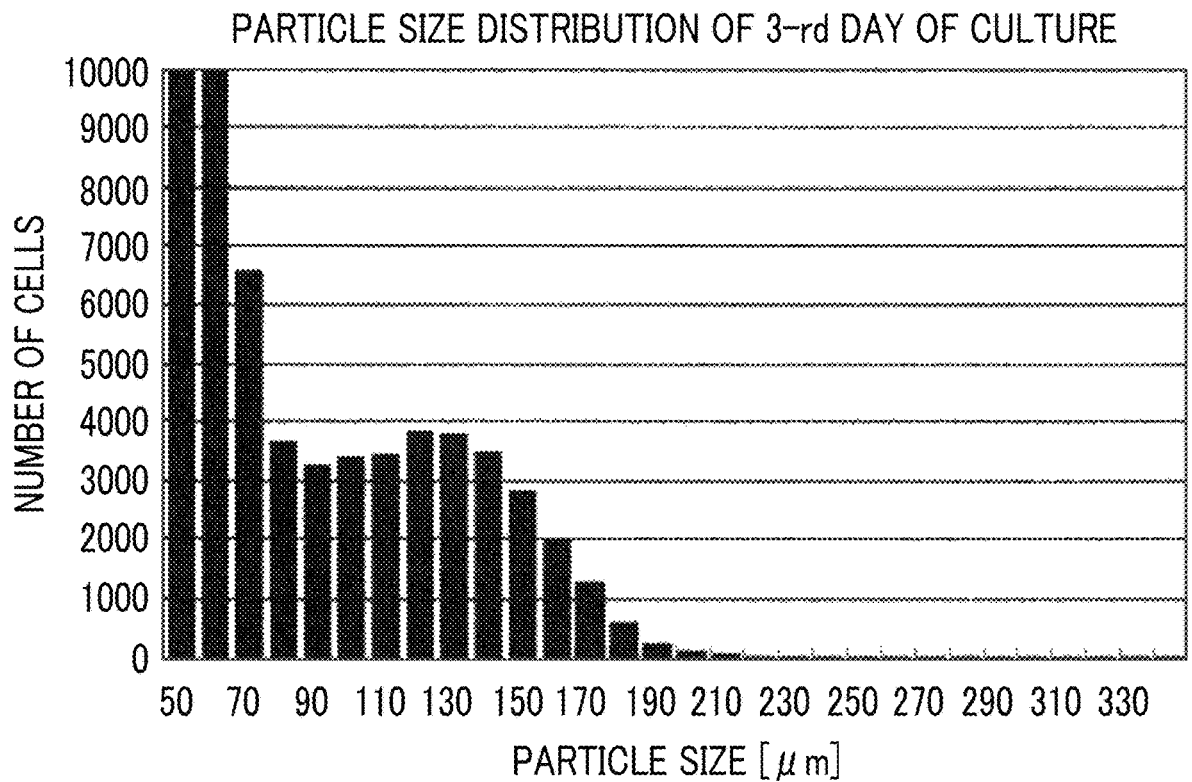
FIG. 17B is a graph showing the particle size distribution of cells and the like that is acquired at a different timing during one cycle period of the culture performed by the cell culture apparatus according to the embodiment of the technique of the disclosure.
Figure 17C:
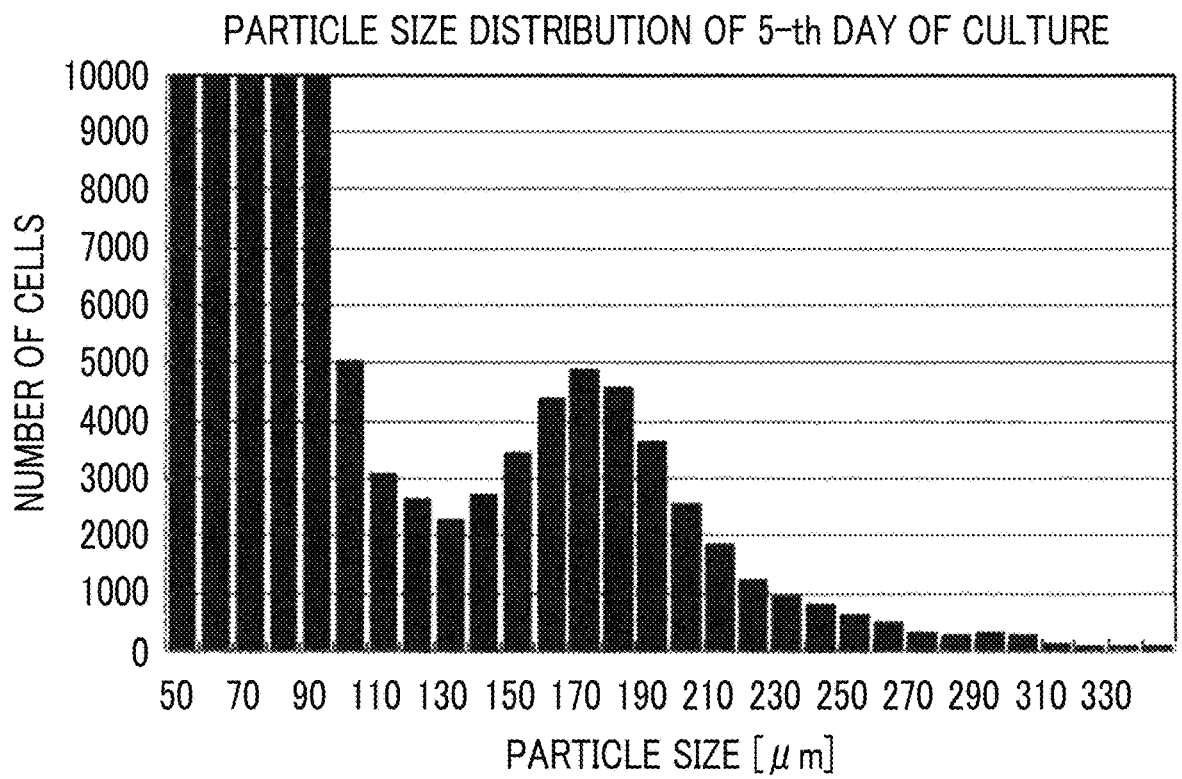
FIG. 17C is a graph showing the particle size distribution of cells and the like that is acquired at a different timing during one cycle period of the culture performed by the cell culture apparatus according to the embodiment of the technique of the disclosure.

FIGS. 17A, 17B, and 17C are graphs showing the particle size distributions of cells and the like that are acquired at different timings during one cycle period of the culture performed by the cell culture apparatus 100. In a case where the first day of a culture cycle is defined as 0-th day, FIGS. 17A, 17B, and 17C show the particle size distribution of 1-st day, the particle size distribution of 3-rd day, and the particle size distribution of 5-th day, respectively. Each of the particle size distributions was acquired on the basis of the plurality of images acquired by the imaging unit 10A provided on the upstream side of the mixing unit 150. As apparent from the comparison of the respective particle size distributions shown in FIGS. 17A to 17C, it is found that the peak of the particle size distribution of cell masses is shifted with time in a direction where a particle size is increased. As described above, according to the cell culture apparatus 100 of this embodiment, it is possible to grasp whether or not culture is smoothly performed every day since it is also possible to grasp the temporal change of the particle size distribution of cell masses during one cycle period of culture.

The imaging unit 10 of this embodiment can be used not only to monitor a state in which cells are cultured but also to determine whether or not elements of the cell culture apparatus are suitable for culture. For example, since a tube pump used as liquid feed means for cell suspension can feed liquid in a state where the tube pump is insulated from the external environment, it is difficult for biological contamination to be caused. For this reason, a tube pump is often used as liquid feed means for cell suspension. However, since the tube pump mechanically draws a tube to feed liquid, there is a concern that the tube pump may destroy cell masses. Accordingly, the influence of the tube pump on cell masses was confirmed using the imaging unit 10 according to this embodiment.

Figure 18:
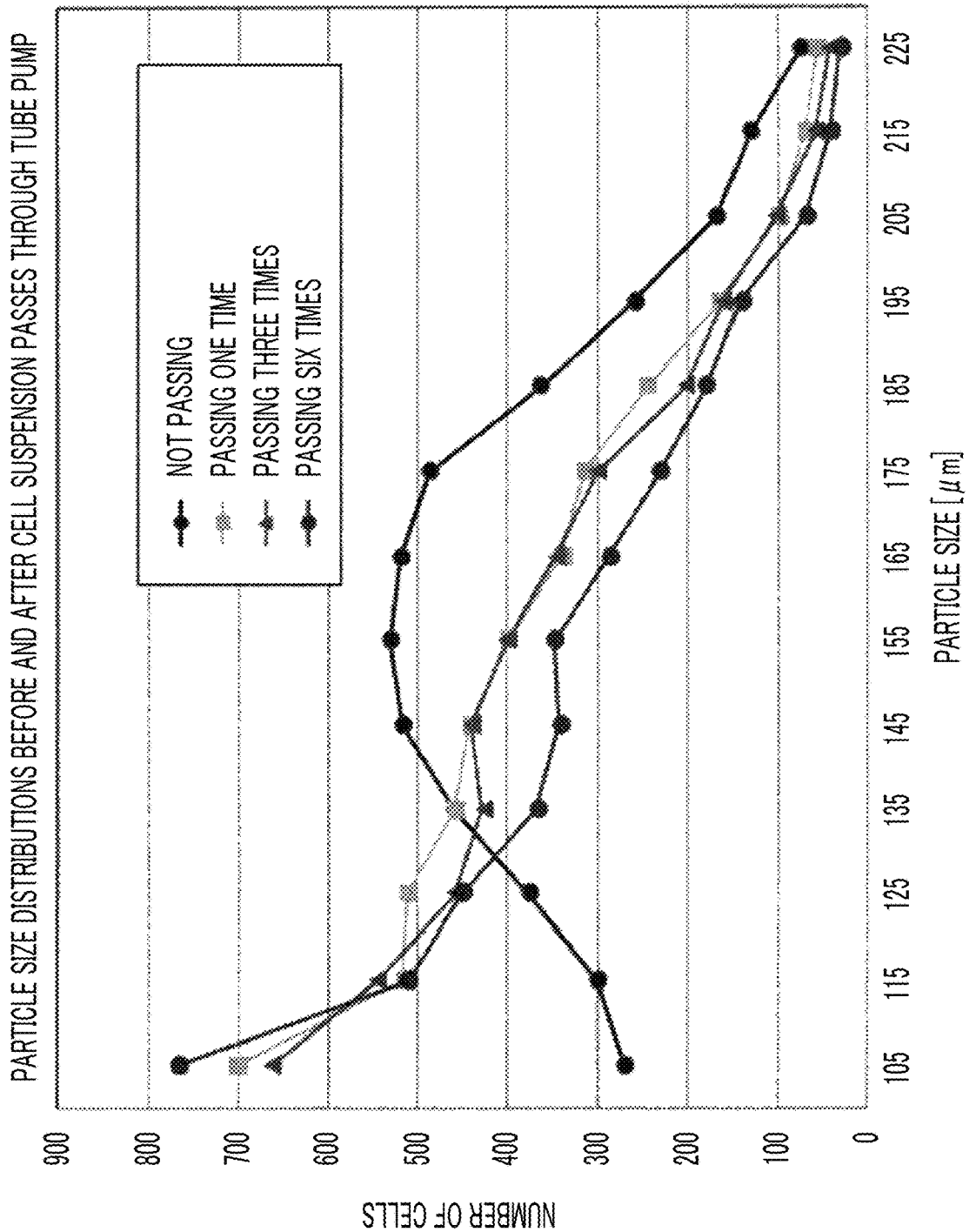
FIG. 18 is a graph showing a result of observation of a change in the particle size distribution of cell masses in a case where the imaging units according to the embodiment of the technique of the disclosure are installed at an inlet and an outlet of a tube pump and cell suspension is made to repeatedly pass through the tube pump.

FIG. 18 is a graph showing a result of observation of a change in the particle size distribution of cell masses in a case where the imaging units 10 according to this embodiment are installed at the inlet and the outlet of the tube pump and cell suspension is made to repeatedly pass through the tube pump. FIG. 18 shows particle size distribution before cell suspension passes through the tube pump (in a case where the number of times of passing of the cell suspension through the tube pump is 0) and the particle size distributions of cell masses after the cell suspension passes through the tube pump one time, three times, and six times.

It is found that the peak of the number of cell masses is present near a particle size of 155 μm before cell suspension passes through the tube pump (in a case where the number of times of passing of cell suspension through the tube pump is 0). It is found that the peak of particle size distribution is shifted in a direction where a particle size is reduced even in a case where cell suspension passes through the tube pump only one time. After that, in a case where cell suspension is made to repeatedly pass through the tube pump, it is found that a change in the particle size distribution is small but the particle size distribution is changed in a direction where a particle size is reduced. From the above-mentioned results, it is possible to deduce that the tube pump crushes cell masses contained in the cell suspension.

As apparent from the above description, according to the cell culture apparatus 100 of this embodiment, the cultured cells are measured on the basis of the plurality of images that are acquired by the imaging unit 10 provided in the middle of the flow passage in which cell suspension flows. Accordingly, an act for collecting cells and the like is unnecessary. Therefore, the risk of biological contamination can be avoided and cells are not consumed. Further, since cultured cells can be automatically measured, efforts and time can be significantly reduced as compared to a manual method in the related art.

Furthermore, according to the cell culture apparatus 100 of this embodiment, since the imaging unit 10 is installed in the middle of the flow passage through which all the cells cultured in the cell culture apparatus 100 pass, all the cells can be used as an object to be measured. Accordingly, the measurement accuracy for cells can be improved as compared to a measurement method in the related art that uses only some collected cells as an object to be measured.

Further, according to the cell culture apparatus 100 of this embodiment, it is possible to visualize the actual states of the respective treatments that are to be performed by the dividing unit 130, the concentrating unit 140, and the mixing unit 150. In other words, it is possible to monitor whether or not the respective treatments to be performed by the dividing unit 130, the concentrating unit 140, and the mixing unit 150 are performed as supposed. Accordingly, since it is possible to early detect the abnormality of each treatment unit, it is possible to quickly take a necessary measure. Furthermore, since it is also possible to early determine whether or not to quit culture in a case where abnormality is detected, the occurrence of unnecessary costs can be minimized.

Moreover, the measurement of cells, which is performed by the imaging unit 10 according to this embodiment, can be used not only during culture but also at the time of startup of the cell culture apparatus. For example, the statistical data acquired by the imaging unit 10 can be used in a case where the treatment conditions of the division treatment, the concentration treatment, and the mixing treatment are to be determined. Since the imaging unit 10 according to this embodiment is used, conditions can be accurately evaluated with saved labor. Accordingly, not only a human test load but also the number of test levels can be reduced. As a result, a test period can be shortened and the costs of a culture solution and cells used for a test can be reduced.

The entire content of the disclosure of Japanese Patent Application No. 2017-015997, filed Jan. 31, 2017, is incorporated in this specification by reference. All documents, patent applications, and technical standards disclosed in this specification are incorporated in this specification by reference so that the incorporation of each of the documents, the patent applications, and the technical standards by reference is specific and is as detailed as each of the documents, the patent applications, and the technical standards.

What is claimed is:

1. A cell culture apparatus comprising:
    a flow passage in which cell suspension containing at least one of cells or cell masses as granular bodies is to flow; and
    an imaging unit that is provided in a middle of the flow passage and continuously images the plurality of granular bodies contained in the cell suspension to acquire a plurality of images while the cell suspension flows in the flow passage,
    wherein the imaging unit includes a flow cell through which the cell suspension is to pass, and an imaging part that includes a plurality of imaging elements of which imaging fields of view are set to the flow cell,
    wherein the flow cell includes an inlet into which the cell suspension is to flow, an outlet out of which the cell suspension flowing in from the inlet is to flow, and a flat flow passage that is provided between the inlet and the outlet and is formed of a member of which a thickness in an optical axis direction of the imaging part is smaller than thicknesses of the inlet and the outlet in the optical axis direction and which has light transmittance, and
    the imaging fields of view are set to the flat flow passage.

2. The cell culture apparatus according to claim 1, further comprising:
    a derivation unit that derives statistical data on the plurality of granular bodies on the basis of the plurality of images.

3. The cell culture apparatus according to claim 2,
    wherein the statistical data includes a total number of cells forming the granular bodies, or the statistical data includes at least one of: (i) a number of granular bodies in each of a plurality of particle size ranges, (ii) a number of granular bodies in each particle size range per unit volume, or (iii) a number of granular bodies, among the plurality of granular bodies, which are in each of a plurality of roundness ranges.

4. The cell culture apparatus according to claim 1,
    wherein the flat flow passage is provided between the inlet and the outlet and is formed of a member of which a thickness in an optical axis direction of the imaging part is smaller than a length in a width direction crossing a flow direction of the cell suspension flowing in the flow cell and which has light transmittance, and
    the imaging fields of view are set to the flat flow passage.

5. The cell culture apparatus according to claim 1,
    wherein the thickness of the flat flow passage in the optical axis direction is uniform.

6. The cell culture apparatus according to any one of claim 1,
    wherein the entire area of the flat flow passage in a width direction crossing a flow direction of the cell suspension is in the imaging fields of view of the plurality of imaging elements.

7. The cell culture apparatus according to claim 1,
    wherein the imaging part includes an area sensor that includes the plurality of imaging elements, and a first telecentric lens that is provided on a light-incident side of the area sensor.

8. The cell culture apparatus according to claim 7,
    wherein the imaging unit further includes an illumination part that irradiates the flat flow passage with illumination light.

9. The cell culture apparatus according to claim 8,
wherein the illumination part includes a light source that emits the illumination light, and a second telecentric lens that is provided on a light-emitting side of the light source.

10. The cell culture apparatus according to claim 9,
wherein an optical axis of the first telecentric lens and an optical axis of the second telecentric lens coincide with each other.

11. The cell culture apparatus according to claim 1,
wherein the imaging part images each of the plurality of granular bodies, which pass through the inside of the flow cell, one or more times.

12. The cell culture apparatus according to claim 1,
wherein a maximum speed of the cell suspension flowing in the flat flow passage is equivalent to maximum speeds of the cell suspension flowing through the inlet and the outlet.

13. The cell culture apparatus according to claim 1, further comprising:
at least one vessel which is connected to the flow passage and in which the cell suspension is stored;
at least one treatment unit that is connected to the flow passage and performs treatment on the cell suspension; and
a pump that generates the flow of cell suspension in the flow passage.

14. The cell culture apparatus according to claim 13,
wherein a dividing unit, which divides the cell masses contained in the cell suspension, is provided as the treatment unit, and
the imaging unit is provided on each of an upstream side and a downstream side of the dividing unit.

15. The cell culture apparatus according to claim 13,
wherein a concentrating unit, which concentrates the cell suspension, is provided as the treatment unit, and
the imaging unit is provided on each of an upstream side and a downstream side of the concentrating unit.

16. The cell culture apparatus according to claim 13,
wherein a mixing unit, which mixes the cell suspension, is provided as the treatment unit, and
the imaging unit is provided on a downstream side of the mixing unit.

17. The cell culture apparatus according to claim 13,
wherein the pump and the imaging unit operate while being interlocked with each other.

18. The cell culture apparatus according to claim 1,
wherein a flow passage area of the cell suspension flowing in the flat flow passage is equivalent to a flow passage area of the cell suspension flowing through the inlet and the outlet.

19. The cell culture apparatus according to claim 1,
wherein a flow passage areas of the inlet, the outlet, and the flat flow passage are 8 $mm^2$ or more.

20. The cell culture apparatus according to claim 1,
wherein the thickness of the imaging part and the thickness of the inlet and the outlet are configured such that the granular bodies passing through the flow cell substantially do not overlap and such that a maximum speed of the cell suspension flowing in the flat flow passage is equivalent to maximum speeds of the cell suspension flowing through the inlet and the outlet.

* * * * *